US006528051B2

(12) United States Patent
Tamarkin et al.

(10) Patent No.: US 6,528,051 B2
(45) Date of Patent: Mar. 4, 2003

(54) METHODS AND COMPOSITIONS FOR ENHANCING IMMUNE RESPONSE

(75) Inventors: Lawrence Tamarkin, Rockville, MD (US); Giulio F. Paciotti, Baltimore, MD (US)

(73) Assignee: CytImmune Sciences, Inc., College Park, MD (US)

( * ) Notice: Subject to any disclaimer, the term of this patent is extended or adjusted under 35 U.S.C. 154(b) by 0 days.

(21) Appl. No.: 09/935,062

(22) Filed: Aug. 22, 2001

(65) Prior Publication Data

US 2002/0071826 A1 Jun. 13, 2002

Related U.S. Application Data

(63) Continuation of application No. 09/189,748, filed on Nov. 10, 1998, now Pat. No. 6,407,218.
(60) Provisional application No. 60/107,455, filed on Nov. 6, 1998, provisional application No. 60/075,811, filed on Feb. 24, 1998, and provisional application No. 60/065,155, filed on Nov. 10, 1997.

(51) Int. Cl.$^7$ .................. A61K 38/00; A61K 38/19
(52) U.S. Cl. .................. 424/85.2; 424/85.1; 424/184.1; 424/649; 424/604; 424/278.1; 514/12
(58) Field of Search .................. 424/85.2, 85.1, 424/184.1, 649, 604, 278.1; 514/12

(56) References Cited

U.S. PATENT DOCUMENTS

| | | | |
|---|---|---|---|
| 2,768,958 A | 10/1956 | Stewart et al. ............. 516/78 |
| 2,785,153 A | 3/1957 | Locke et al. ............... 514/6 |
| 3,145,144 A | 8/1964 | Ando et al. ............. 424/258.1 |
| 3,149,036 A | 9/1964 | Woodhour et al. ........ 424/209.1 |
| 3,269,912 A | 8/1966 | Grafe ..................... 424/212 |
| 3,399,263 A | 8/1968 | Strazdins et al. ........ 424/278.1 |
| 3,531,565 A | 9/1970 | Webb et al. ............... 424/239 |
| 3,577,523 A | 5/1971 | Stolar et al. ............ 424/278.1 |
| 3,651,211 A | 3/1972 | Gillchriest et al. ....... 424/217.1 |
| 3,819,820 A | 6/1974 | Lorina et al. .............. 424/1.29 |
| 3,919,413 A | 11/1975 | Mebus ..................... 424/221.1 |
| 3,983,228 A | 9/1976 | Woodhour et al. ........ 424/212.1 |
| 4,016,252 A | 4/1977 | Relyveld ................. 424/212.1 |
| 4,053,587 A | 10/1977 | Davidson et al. ........... 424/649 |
| 4,069,313 A | 1/1978 | Woodhour et al. ........ 424/209.1 |
| 4,177,263 A | 12/1979 | Rosenburg et al. ......... 436/539 |
| 4,196,185 A | 4/1980 | Focella et al. ............ 530/389.8 |
| 4,197,237 A | 4/1980 | Leute et al. ............... 436/542 |
| 4,197,286 A | 4/1980 | Rao ....................... 530/389.8 |
| 4,213,964 A | 7/1980 | Buckler .................... 530/379 |
| 4,215,036 A | 7/1980 | Malley .................... 530/389.2 |
| 4,218,436 A | 8/1980 | Fitzpatrick .............. 530/389.9 |
| 4,329,281 A | 5/1982 | Christenson et al. |
| 4,330,530 A | 5/1982 | Baker |
| 4,332,787 A | 6/1982 | Homcy et al. |
| 4,339,437 A | 7/1982 | Rosenberg et al. |
| 4,346,074 A | 8/1982 | Gilmour et al. |
| 4,451,570 A | 5/1984 | Royston et al. |
| 4,487,780 A | 12/1984 | Scheinberg |
| 4,578,270 A | 3/1986 | Csizer et al. |
| 4,594,325 A | 6/1986 | Lundak |
| 4,608,252 A | 8/1986 | Khanna et al. |
| 4,624,921 A | 11/1986 | Larrick et al. |
| 4,624,923 A | 11/1986 | Margel |
| 4,639,336 A | 1/1987 | Jouguey et al. |
| 4,657,763 A | 4/1987 | Finkelstein |
| 4,693,975 A | 9/1987 | Kozbor et al. |
| 4,720,459 A | 1/1988 | Winkelhake |
| 4,740,589 A | 4/1988 | Moreno |
| 4,744,760 A | 5/1988 | Molday |
| 4,753,873 A | 6/1988 | Beltz et al. |
| 4,812,556 A | 3/1989 | Vahlne et al. |
| 4,880,750 A | 11/1989 | Francoeur |
| 4,882,423 A | 11/1989 | Taguchi et al. |
| 4,906,564 A | 3/1990 | Lyon et al. |

(List continued on next page.)

FOREIGN PATENT DOCUMENTS

| | | |
|---|---|---|
| EP | 0 044 722 | 1/1982 |
| EP | 0 156 242 | 3/1985 |
| EP | 0 179 83 | 4/1986 |
| EP | 0 269 408 | 11/1987 |
| EP | 0 667 398 | 8/1995 |
| FR | 2 334 366 | 7/1977 |
| FR | 2 533 827 | 4/1984 |
| GB | 981242 | 1/1965 |
| WO | WO 91/02078 | 2/1991 |
| WO | WO 94/21288 | 9/1994 |
| WO | WO 96/04313 | 2/1996 |

OTHER PUBLICATIONS

Balkwill, et al., "The Cytokine Network," *Immun. Today*, vol. 10, No. 9, pp. 299–304 (1989).

(List continued on next page.)

*Primary Examiner*—Yvonne Eyler
*Assistant Examiner*—Fozia Hamud
(74) *Attorney, Agent, or Firm*—Kilpatrick Stockton LLP

(57) ABSTRACT

The methods and compositions of the present invention are directed to enhancing an immune response and increasing vaccine efficacy through the simultaneous or sequential targeting of specific immune system components. More particularly, specific immune components, such as macrophages, dendritic cells, B cells and T cells, are individually activated by component-specific immunostimulating agents. One such component-specific immunostimulating agent is an antigen-specific, species-specific monoclonal antibody. The invention is also directed to a method for the in vitro production of the antigen-specific, species-specific monoclonal antibodies which relies upon the in vitro conversion of blood-borne immune cells, such as macrophages and lymphocytes. Vaccine efficacy is enhanced by the administration of compositions containing component-specific immunostimulating agents and other elements, such as antigens or carrier particles, such as colloidal methods, such as gold.

18 Claims, 11 Drawing Sheets

(3 of 11 Drawing Sheet(s) Filed in Color)

U.S. PATENT DOCUMENTS

| | | | |
|---|---|---|---|
| 4,977,286 A | 12/1990 | Nicolaou et al. | |
| 5,017,687 A | 5/1991 | Vahlne et al. | |
| 5,019,497 A | 5/1991 | Olsson | |
| 5,035,995 A | 7/1991 | Taguchi et al. | |
| 5,112,606 A | 5/1992 | Shiosaka et al. | |
| 5,126,253 A | 6/1992 | Nakanishi et al. | |

OTHER PUBLICATIONS

Coulombe et al., "Cytochemical Demonstration of Increased Phospholipid Content in Cell Membranes in Chlorphrntermine–induced Phospholipidosis," *Journal of Histochemistry and Cytochemistry,* vol. 37, No. 2, pp. 139–147 (1989).

Fraker, et al., "Passive Immunization Against Tumor Necrosis Factor Partially Abrogates Interleukin 2 Toxicity," *The Journal of Experimental Medicine,* vol. 170, pp. 1015–1020 (1989).

Goldstein, et al., "Cardiovascular Effects of Platelet–Activating Factor," *Lipids,* vol. 26, No. 212, pp. 1250–1256 (1991).

Hashimoto, et al., "Action Site of Circulating Interleukin 1 on the Rabbit Brain," *Brain Research,* vol. 540, pp. 217–223 (1991).

Hisamatsu et al., "Platelet Activating Factor Induced Respiratory Mucosal Damage", *Lipids,* vol. 26, No. 12, pp. 1287–1291 (1991).

Hopkins, et al., "Early Events Following the Binding Epidermal Growth Factor to Surface Receptors on Ovarian Granulosa Cells," European Journal of Cell Biology, vol. 48, pp. 316–332 (1990).

Kang, et al., "Ultrastructural and Immunocytochemical Study of the Uptake and Distribution of Bacterial Lipopolysaccharide in Human Monocytes," Journal of Leukocyte Biology, vol. 48, pp. 316–332 (1990).

Kirchner, et al., "The Development of Neutralizing Antibodies in a Patient Receiving Subcutaneous Recombinant and Natural Interleukin–2," *Cancer,* No. 7, vol. 67, pp. 1862–1864 (1991).

Lanzavecchia, "Identifying Strategies for Immune Intervention," *Science,* vol. 260, pp. 937–944 (1993).

Morris, et al., Validation of the Biotinyl Ligand–Avidin–Gold Technique, "The Journal of Histochemistry and Cyrochemistry," vol. 40, No. 5, pp. 711–721 (1992).

Ohmann et al., "Expression of Tumor Necrosis Factor☐ Receptors on Bovine Macrophages, Lymphocytes and Polymorphonuclear Leukocytes, Internalization of Receptor–Bound Ligand, and Some Functional Effects," *Lymphokine Research,* vol. 9, No. 1, pp. 43–58 (1990).

Paciotti, G.F., et al. "Interleukin–1 Directly Regulates Hormone–Dependent Human Breast Cancer Cell Proliferation In–Vitro," *Mol. Endocrinol.,* vol. 2, pp. 459–464 (1988).*

Paciotti, G.F., et al. "Interleukin–1α Differentially Synchronizes Estrogen–Dependent and Estrogen–Independent Human Breast Cancer Cells in the $G_0/G_1$ I Phase of the Cell Cycle," *Anticancer Research,* vol. 11, pp. 25–32 (1991).*

Paciotti, G.F., et al. "Interleukin–2 Differentially Effects the Proliferation of a Hormone–Dependent and a Hormone–Independent Human Breast Cancer Cell Line in Vitro and In Vivo," *Anticancer Research,* vol. 8, pp. 1233–1240 (1988).*

Peters, et al., "Binding and Internalization of Biotinylated Interleukin–2 in Human Lymphocytes," Blood, vol. 76, No. 1, pp. 97–104 (1990).*

Roitt, et al., *Immunology,* Mosby, (Baltimore, MD), $3^{rd}$ ed., (1993).*

Tomii, et al., "Production of Anti–Platelet–Activating Factor Antibodies by the Use of Colloidal Gold as Carrier," *Jpn. J. Med. Sci. Biol.* vol. 44, pp. 75–80 (1991).*

\* cited by examiner

Fig_1

Fig_2

Fig_3

Fig_4

FIG_8

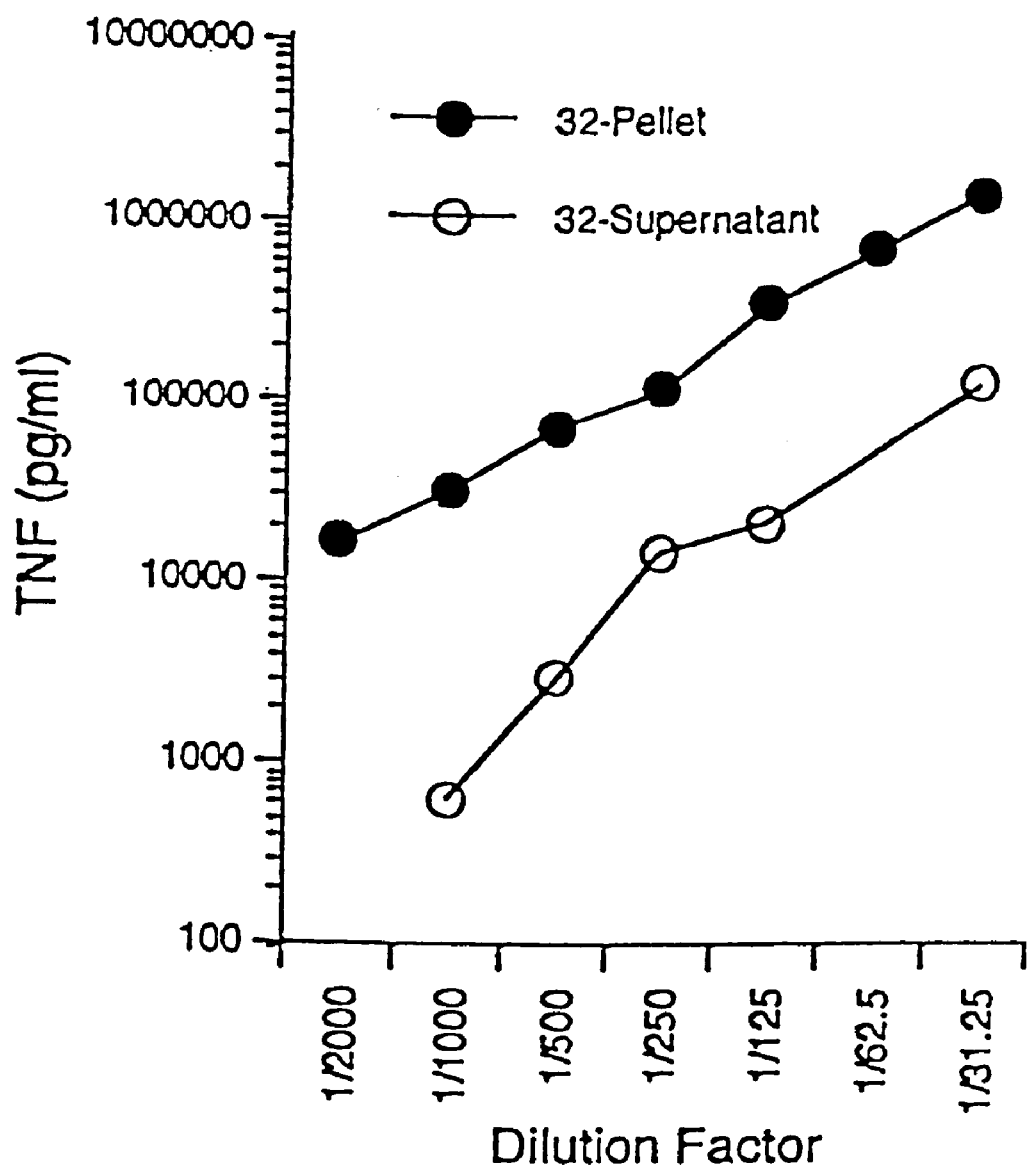
Fig_10

METHODS AND COMPOSITIONS FOR ENHANCING IMMUNE RESPONSE

CROSS-REFERENCE TO RELATED APPLICATIONS

This application is a continuation of U.S. application Ser. No. 09/189,748, filed on Nov. 10, 1998, now U.S. Pat. No. 6,407,218 further claims the benefit of U.S. Provisional Application No. 60/107,455, filed Nov. 6, 1998, U.S. Provisional Application No. 60/075,811, filed Feb. 24, 1998, and of U.S. Provisional Application No. 60/065,155 filed Nov. 10, 1997.

FIELD OF THE INVENTION

The present invention relates generally to immunology. More specifically, the invention relates to methods and compositions for the enhancement of an immune response in a human or animal. Such enhancement may result in stimulation or suppression of the immune response. The invention also relates to targeted component-stimulating compositions that easily and efficiently present antigenic components to particular immune cells to enhance an immune response in a human or animal. The present invention further relates to the use of such methods and compositions for the production of antigen-specific, species-specific monoclonal antibodies and the in vitro methods for production of such antibodies.

BACKGROUND OF THE INVENTION

The introduction of desired agents into specific target cells has been a challenge to scientists for a long time. The challenge of specific targeting of agents is to get an adequate amount of the agent or the correct agent to the target cells of an organism without providing too much exposure of the rest of the organism. A very desired target for delivery of specific agents is the selective control of the immune system. The immune system is a complex response system of the body that involves many different kinds of cells that have differing activities. Activation of one portion of the immune system usually causes many different responses due to unwanted activation of other related portions of the system. Currently, there are no methods or compositions for producing the desired response by targeting the specific components of the immune system.

One method that has been used with limited success is the targeting of cells that bear a specific receptor and providing an antibody to that receptor that acts as a carrier for an agent. The agent could be a pharmaceutical agent that is a cell stimulant or the therapeutic agent could be a radioactive moiety that causes cell death. The problems inherent in this techniques are the isolation of the specific receptor, the production of an antibody having selective activity for that receptor and no cross-reactivities with other similar epitopes, and attachment of the agent to the antibody. A problem attendant to such limited delivery is that the agent may never be released internally in the targeted cell, the agent is not releasably bound to the antibody and therefore, may not be fully active or capable of any activity once it is delivered to the site.

The immune system is a complex interactive system of the body that involves a wide variety of components, including cells, cellular factors which interact with stimuli from both inside the body and outside the body. Aside from its direct action, the immune system's response is also influenced by other systems of the body including the nervous, respiratory, circulatory and digestive systems.

One of the better known aspects of the immune system is its ability to respond to foreign antigens presented by invading organisms, cellular changes within the body, or from vaccination. Some of the first kinds of cells that respond to such activation of the immune system are phagocytes and natural killer cells. Phagocytes include among other cells, monocytes, macrophages, and polymorphonuclear neutrophils. These cells generally bind to the foreign antigen, internalize it and may destroy it. They also produce soluble molecules that mediate other immune responses, such as inflammatory responses. Natural killer cells can recognize and destroy certain virally-infected embryonic and tumor cells. Other factors of the immune response include both complement pathways which are capable of responding independently to foreign antigens or acting in concert with cells or antibodies.

One of the aspects of the immune system that is important for vaccination is the specific response of the immune system to a particular pathogen or foreign antigen. Part of the response includes the establishment of "memory" for that foreign antigen. Upon a secondary exposure, the memory function allows for a quicker and generally greater response to the foreign antigen. Lymphocytes in concert with other cells and factors, play a major role in both the memory function and the response.

Generally, it is thought that the response to antigens involves both humoral responses and cellular responses. Humoral immune responses are mediated by non cellular factors that are released by cells and which may or may not be found free in the plasma or intracellular fluids. A major component of a humoral response of the immune system is mediated by antibodies produced by B lymphocytes. Cell-mediated immune responses result from the interactions of cells, including antigen presenting cells and B lymphocytes (B cells) and T lymphocytes (T cells).

The response is initiated by the recognition of foreign antigens by various kinds of cells, principally macrophages or other antigen presenting cells. This leads to activation of lymphocytes, in particular, the lymphocytes that specifically recognize that particular foreign antigen and results in the development of the immune response, and possibly, elimination of the foreign antigen. Overlaying the immune response directed at elimination of the foreign antigen are complex interactions that lead to helper functions, stimulator functions, suppresser functions and other responses. The power of the immune system's responses must be carefully controlled at multiple sites for stimulation and suppression or the response will either not occur, over respond or not cease after elimination.

The recognition phase of response to foreign antigens consists of the binding of foreign antigens to specific receptors on immune cells. These receptors generally exist prior to antigen exposure. Recognition can also include interaction with the antigen by macrophage-like cells or by recognition by factors within serum or bodily fluids.

In the activation phase, lymphocytes undergo at least two major changes. They proliferate, leading to expansion of the clones of antigen-specific lymphocytes and amplification of the response, and the progeny of antigen-stimulated lymphocytes differentiate either into effector cells or into memory cells that survive, ready to respond to re-exposure to the antigen. There are numerous amplification mechanisms that enhance this response.

In the effector phase, activated lymphocytes perform the functions that may lead to elimination of the antigen or establishment of the vaccine response. Such functions include cellular responses, such as regulatory, helper, stimulator, suppressor or memory functions. Many effector functions require the combined participation of cells and cellular factors. For instance, antibodies bind to foreign antigens and enhance their phagocytosis by blood neutrophils and mononuclear phagocytes. Complement pathways are activated and may participate in the lysis and phagocytosis of microbes in addition to triggering other body responses, such as fever.

In the immune response to antigens, immune cells interact with each other by direct cell to cell contact or indirect cell to cell (factor mediated) communication. For example, interactions between T cells, macrophages, dendritic cells, and B cells are necessary for an effective immune response. B and T cells are activated by signals from dendritic cells or macrophages, which are antigen presenting cells (APC) that present antigens and deliver activation signals to resting cells. Activated T cells help control immune responses and participate in the removal of foreign organisms. Helper T cells cause cells to become better effector cells, such as helping cytotoxic T cell precursors, to develop into killer cells, helping B cells make antibodies, and helping increase functions of other cells like macrophages. Activated B cells divide and produce antigen specific antibodies and memory B cells. The cells involved in the immune response also secrete cellular factors or cytokines, which enhance the functions of phagocytes, stimulate inflammatory responses and effect a variety of cells.

The reactions of these cells also involve feedback loops. Macrophages and other mononuclear phagocytes, or APCs, actively phagocytose antigens for presentation to B and T cells and such activity can be enhanced by lymphocytic cellular factors. Macrophages also produce cytokines that, among other activities, stimulate T cell proliferation and differentiation, and that recruit other inflammatory cells, especially neutrophils, and are responsible for many of the systemic effects of inflammation, such as fever. One such cytokine, called interleukin-12, is especially important for the development of cell-mediated immunity.

Dendritic cells are also APCs which initiate an immune response. There are a number of different types of dendritic cells, including lymphoid dendritic cells and Langerhans cells of the skin. They can be found throughout the body and particularly in the spleen, lymph nodes, tonsils, Peyer's patches, and thymus. They are irregularly shaped cells which continuously extend and contract dendritic (tree-like) processes. One of their roles in the immune system is to regulate and induce B and T cell activation and differentiation. They are potent accessory cells for the development of cytotoxic T cells, antibody formation by B cells, and some polyclonal responses like oxidative mitogenesis. They also stimulate T cells to release the cytokine interleukin-2.

An important arm of vaccination is the response to antigens that is provided by B lymphocytes or B cells. B cells represent about 5 to 15% of the circulating lymphocytes. B cells produce immunoglobulins, IgG, IgM, IgA, IgD, and IgE, which may be released into body fluids, secreted with attached proteins or be inserted into the surface membrane of the B cell. Such immobilized immunoglobulins act as specific antigen receptors. In responding to antigen, these immunoglobulin receptors are crosslinked, known as capping, followed by internalization and degradation of the immunoglobulin. Capping also occurs with glycoproteins located on the surface membrane of the B cells.

The B plasma cells produce and secrete antibody molecules that can bind foreign proteins, polysaccharides, lipids, or other chemicals in extra cellular or cell-associated forms. The antibodies produced by a single plasma cell are specific for one antigen. The secreted antibodies bind the antigen and trigger the mechanisms that facilitate their destruction.

Monoclonal Antibodies

One of the most widely employed aspects of the immune response capabilities is the production of monoclonal antibodies. The advent of monoclonal antibody (Mab) technology in the mid 1 970s provided a valuable new therapeutic and diagnostic tool. For the first time, researchers and clinicians had access to unlimited quantities of uniform antibodies capable of binding to a predetermined antigenic site and having various immunological effector functions. Currently, the techniques for production of monoclonal antibodies is well known in the art.

These monoclonal antibodies were thought to hold great promise in medicine and diagnostics. Unfortunately, the development of therapeutic products based on these proteins has been limited because of problems that are inherent in monoclonal antibody therapy. For example, most monoclonal antibodies are mouse derived and, thus, do not fix human complement well. They also lack other important immunoglobulin functional characteristics when used in humans.

The biggest drawback to the use of monoclonal antibodies is the fact that nonhuman monoclonal antibodies are immunogenic when injected into a human patient. After injection of a foreign antibody, the immune response mounted by a patient can be quite strong. The immune response causes the quick elimination of the foreign antibody, essentially eliminating the antibody's therapeutic utility after an initial treatment. Unfortunately, once the immune system is primed to respond to foreign antibodies, later treatments with the same or different nonhuman antibodies can be ineffective or even dangerous because of cross-reactivity.

Mice can be readily immunized with foreign antigens to produce a broad spectrum of high affinity antibodies. However, the introduction of murine antibodies into humans results in the production of a human-anti-mouse antibody (HAMA) response due to the presentation of a foreign protein in the body. Use of murine antibodies in a patient is generally limited to a term of days or weeks Longer treatment periods may result in anaphylaxis. Moreover, once HAMA has developed in a patient, it often prevents the future use of murine antibodies for diagnostic or therapeutic purposes.

To overcome the problem of HAMA response, researchers have attempted several approaches to modify nonhuman antibodies, to make them human-like. These approaches include mouse/human chimers, humanization, and primatization. Early work in making more human-like antibodies used combined rabbit and human antibodies. The protein subunits of antibodies, rabbit Fab fragments and human Fc fragments, were joined through protein disulfide bonds to form new, artificial protein molecules or chimeric antibodies.

Recombinant molecular biological techniques have been used to create chimeric antibodies. Recombinant DNA technology was used to construct a gene fusion between DNA sequences encoding mouse antibody variable light and heavy chain domains and human antibody light chain (LC) and heavy chain (HC) constant domains to permit expression of chimeric antibodies. These chimeric antibodies contain a large number of nonhuman amino acid sequences and are immunogenic to humans. Patients exposed to these chimeric antibodies produce human-antichimera antibodies (HACA). HACA is directed against the murine V region and can also be directed against the novel V-region/C-region (constant region) junctions present in recombinant chimeric antibodies.

To overcome some of the limitations presented by the immunogenicity of chimeric antibodies, molecular biology techniques are used to created humanized or reshaped antibodies. The DNA sequences encoding the antigen binding portions or complementarity determining regions (CDRs) of murine monoclonal antibodies are grafted, by molecular means, on the DNA sequences encoding the frameworks of human antibody heavy and light chains. The humanized Mabs contain a larger percentage of human antibody sequences than do chimeric Mabs. The end product, which comprises approximately 90% human antibody and 10% mouse antibody, contains a mouse binding site on an human antibody. It also contains certain amino acid substitutions from the mouse Mab into the framework of the humanized Mab in order to retain the correct shape, and thus, binding affinity for thetarget antigen.

In practice, simply substituting murine CDRs for human CDRs is not sufficient to generate efficacious humanized antibodies retaining the specificity of the original murine antibody. There is an additional requirement for the inclusion of a small number of critical murine antibody residues in the human variable region. The identity of these residues depends upon the structure of both the original murine antibody and the acceptor human antibody. It is the presence of these murine antibody residues that helps create a HACA response in the patient, leading to rapid clearance of the monoclonal antibodies and the fear of anaphylaxis.

Another technique, called resurfacing technology, is used for humanizing mouse antibodies. Resurfacing involves replacing the mouse antibody surface with a human antibody surface in a process that is faster and more efficient than other humanization techniques. This technique provides a method of redesigning murine monoclonal antibodies to resemble human antibodies by humanizing only those amino acids that are accessible at the surface of the V-regions of the recombinant Fv. The resurfacing of murine monoclonal antibodies may maintain the avidity of the original mouse monoclonal antibody in the reshaped version, because the natural framework-CDR interactions are retained. Again, these antibodies suffer from the problem of being antigenic due to their mouse origins.

Other technologies use primate, rather than mouse, sequences to humanize Mabs. The rationale of this approach, called primatization, is that most of the sequences in the primate antibody variable region are indistinguishable from human sequences. Primatized anti-CD4 Mabs for the treatment of rhumatoid arthritis and severe asthma are being developed. However, these Mabs are still foreign proteins to the immune system of the patient and evoke an immune response.

In an effort to avoid the immune response to foreign proteins, a variety of approaches are being developed to make human Mabs that contain only human antibody components. One approach is to isolate a human B cell clone that naturally makes antibody to the desired antigen and grow it in a trioma cell culture system. Because human antibodies are made only against antigens that are foreign to thehost, none of the human B cells will make antibodies against human antigens. Therefore, this approach is not useful to produce Mabs against antigens that are human proteins.

Two other approaches to create human Mabs are phage display and use of transgenic mice. Phage display technique takes advantage of the ability of humans to make antibodies against any possible structure. This technique uses the antibody genes from many individual humans to create a large library of phage antibodies, each displaying a functional antibody variable domain on its surface. From this library, individual variable domains are selected for their ability to bind to the desired antigen. The Mab is created through molecular biology techniques by combining an antibody variable domain having the desired binding characteristics and a constant domain that best meets the potential human therapeutic product. Again, this technique lacks antigen specificity. The phage library cannot contain every binding region for any and all desired antigens. It also may contain binding regions which lack specificity. Thus, this technique may require considerable engineering to increase antibody affinities to useful levels.

Transgenic mice are also being used to create "human" antibodies. The transgenic mice are created by replacing mouse immunoglobulin gene loci with human immunoglobulin loci. This approach may provide advantages over phage display technologies because it takes advantages of mouse in vivo affinity maturation machinery.

All of the current technologies for producing human or human-like Mabs are insufficient to provide a species specific antibody that is antigen specific for a described antigen. Chimeric antibodies have the advantages of retaining the specificity of the murine antibody and stimulating human Fc dependent complement fixation and cell-mediated cytotoxicity. However, the murine variable regions of these chimeric antibodies can still elicit a HAMA response, thereby limiting the value of chimeric antibodies as diagnostic and therapeutic agents.

Efforts to immortalize human B-cells or to generate human hybridomas capable of producing immunoglobulins against a desired antigen have been generally unsuccessful, particularly with human antigens. Additionally, immune tolerance in humans prevents the successful generation of antibodies to self-antigens.

Vaccine Therapy

Vaccines may be directed at any foreign antigen, whether from another organism, a changed cell, or induced foreign attributes in a normal "self" cell. The route of administration of the foreign antigen can help determine the type of immune response generated. For example, delivery of antigens to mucosal surfaces, such as oral inoculation with live polio virus, stimulates the immune system to produce an immune response at the mucosal surface. Injection of antigen into muscle tissue often promotes the production of a long lasting IgG response.

Vaccines may be generally divided into two types, whole and subunit vaccines. Whole vaccines may be produced from viruses or microorganisms which have been inactivated or attenuated or have been killed. Live attenuated vaccines have the advantage of mimicking the natural infection enough to trigger an immune response similar to the response to the wild-type organism. Such vaccines generally provide a high level of protection, especially if administered by a natural route, and some may only require one dose to confer immunity. Another advantage of some attenuated vaccines is that they provide person-to-person passage among members of the population. These advantages, however, are balanced with several disadvantages.

Some attenuated vaccines have a limited shelf-life and cannot withstand storage in tropical environments. There is also a possibility that the vaccine will revert to the virulent wild-type of the organism, causing harmful, even life-threatening, illness. The use of attenuated vaccines is contraindicated in immunodeficient states, such as AIDS, and in pregnancy.

Killed vaccines are safer in that they cannot revert to virulence. They are generally more stable during transport and storage and are acceptable for use in immunocompromised patients. However, they are less effective than the live attenuated vaccines, usually requiring more than one dose. Additionally, they do not provide for person-to-person passage among members of the population.

Production of subunit vaccines require knowledge about the epitopes of the microorganism or cells to which the vaccine should be directed. Other considerations in designing subunit vaccines are the size of the subunit and how well the subunit represents all of the strains of the microorganism or cell. The current focus for development of bacterial vaccines has shifted to the generation of subunit vaccines because of the problems encountered in producing whole bacterial vaccines and the side effects associated with their use. Such vaccines include a typhoid vaccine based upon the Vi capsular polysaccharide and the Hib vaccine to *Haemophilus influenzae*.

Other vaccines which have been developed include combination vaccines and DNA vaccines. An example of a combination vaccine is the *Bordetella pertussis* toxin and its surface fimbrial hemaglutinin. In DNA vaccination, the patient is administered nucleic acids encoding a protein antigen that is then transcribed, translated and expressed in some form to produce strong, long-lived humoral and cell mediated immune responses to the antigen. The nucleic acids may be administered using viral vectors or other vectors, such as liposomes.

The immune response created by vaccines can be non-specifically enhanced by the use of adjuvants. These are a heterogeneous group of compounds or carrier components, such as liposomes, emulsions or microspheres, with several different mechanisms of action.

In addition to the typical use of vaccines for protection against disease, vaccination is being used to fight cancer. The idea of non-specifically stimulating the immune system to reject tumors is nearly a century old. Coley, an early reseacher in the field, used bacterial filtrates with considerable success. Attempts to vaccinate against cancer with purified cytokines and immunostimulants have had only limited success and have been effective for only a few types of tumors.

Many diseases, in addition to cancer, are mediated by the immune system. The diseases include allergies, eczema, rhinitis, urticaria, anaphylaxis, transplant rejection, such as kidney, heart, pancreas, lung, bone, and liver transplants; rheumatic diseases, systemic lupus erthematosus, rheumatoid arthritis, seronegative spondylarthritides, sjogren's syndrome, systemic sclerosis, polymyositis, dermatomyositis, type I diabetes mellitus, acquired immune deficiency syndrome, Hashimoto's thyroiditis, Graves' disease, Addison's disease, polyendocrine autoimmune disease, hepatitis, sclerosing cholangitis, primary biliary cirrhosis, pernicious anemia, coeliac disease, antibody-mediated nephritis, glomerulonephritis, Wegener's granulomatosis, microscopic polyarteritis, polyarteritis nodosa, pemphigus, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, Bruton's syndrome, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, and non-Hodgkin's lymphoma.

Because of the safety concerns associated with the use of attenuated vaccines and the low efficacy of killed vaccines, there is a need in the art for compositions and methods that enhance vaccine efficacy. There is also a need in the art for compositions and methods of enhancing the immune system which stimulate both humoral and cell-mediated responses. There is a further need in the art for the selective adjustment of an immune response and manipulating the various components of the immune system to produce a desired response. Additionally, there is a need for methods and compositions that can accelerate and expand the immune response for a more rapid response in activation. There is an increased need for the ability to vaccinate populations, of both humans and animals, with vaccines that provide protection with just one dose.

What is needed are compositions and methods for target specific delivery of agents to only the target cells. It would be preferable for some administrations and treatments if the agent is internalized by the targeted cells. Once inside the cell, the agent should be sufficiently released from the transport system such that the agent is active. Such compositions and methods should be able to deliver therapeutic agents to the target cells efficiently. What is also needed are compositions and methods that can be used both in in vitro and in vivo systems.

There is also a general need for compositions of antigen specific, species specific antibodies and improved methods for producing them. There is a particular need for methods for producing completely human antibodies having affinity for a predetermined antigen. These human immunoglobulins should be easily and economically produced in a manner suitable for therapeutic and diagnostic formulation.

SUMMARY OF THE INVENTION

The present invention comprises methods and compositions for targeted delivery of component-specific immunostimulating molecules to individual immune cells. These component-specilic immunostimulating molecules bind and stimulate specific immune cells because of specific receptors on the cells. Thus, in a mixture of different cell types, the component-specific immunostimulating molecules are bound only by cells having the selected receptor, and cells lacking the receptor are unaffected. In some populations of immune cells, only one cell type contains receptors that bind a given component-specific immunostimulating agent. In other cell populations, multiple immune cells may contain the receptor that binds the component-specific immunostimulating agent. It is also possible for a given cell type to contain receptors for multiple component-specific immunostimulating agents.

The methods of targeted delivery to the immune cells may be such methods as those used for in vitro techniques such as addition to cellular cultures or media or those used for in vivo administration. In vivo administration may include direct application to the cells or such routes of administration as used for delivery of vaccines to humans, animals, or other organisms.

In one embodiment, the present invention comprises methods and compositions for the simultaneous and/or sequential targeted stimulation of specific individual components of the immune system by a putative antigen or vaccine molecule to enhance, alter, or suppress the immune response to the antigen/vaccine. Another aspect of the invention provides for increasing the efficacy with which antigens and vaccines induce an immune response. In one embodiment, the methods and compositions of the invention are capable of the simultaneous stimulation of many different individual immune components through the presentation of specific component-stimulating compositions.

The present invention also comprises compositions and methods for the sequential stimulation of the immune system by providing component-stimulating compositions at one or more steps in an immune response cascade of interacting factors and cells. In one disclosed embodiment, the specific immune components stimulated are macrophages, dendritic cells, B cells, and T cells.

In a preferred embodiment, the methods comprise the sequential administration of component-stimulating compositions. The compositions may comprise the same component-specific immunostimulating agent given at different times or by different methods of administration, such as orally the first time and by injection the second time. In another preferred embodiment, the methods comprise the sequential administration of different component-specific immunostimulating agents. For example, a first component-specific immunostimulating agent will stimulate an initiating step of the immune response, followed by a later administration of a second component-specific immunostimulating agent to stimulate a later step of the immune response. The present invention contemplates administration of multiple component-specific immunostimulating agents to initiate several pathways of the immune system, followed by later administrations of the same or other component-specific immunostimulating agents to continue and enhance the immune response.

Additionally, it is contemplated in the present invention that the compositions and methods described herein can be used for stimulation of an immune response or the suppression of an immune response. Administration of component-specific immunostimulating agents for the suppression of immune responses can be used to control autoimmune diseases or organ rejection.

In another embodiment, the present invention comprises methods and compositions for the production of antigen-specific, speciespecific monoclonal antibodies. These methods and compositions rely upon the conversion of immune cells. In a preferred embodiment, the methods and compositions comprise thein vitro conversion of circulating immune cells. These cells mount a primary response to the antigen, resulting in the production of antigen specific antibody. These selected primary clones are then immortalized to produce cells that secrete antibodies comprised entirely of protein from the selected species.

In a preferred embodiment of the invention the antibodies produced are wholly human monoclonal antibodies which are produced through the in vitro culturing of human peripheral blood lymphocytes. A key element to this invention is the antigenic recognition of "self" molecules. Such self molecules include those molecules that are native or naturally occurring in an individual, as well as any molecule having a structure which is the same as that which occurs naturally in a particular species. This recognition reduces immunogenicity because the antibodies contain protein from only one species.

These antibodies, however, may still result in some immunogenicity because the protein contained within the antibody, while from the same species, is foreign to the individual. In another preferred embodiment, the monoclonal antibodies produced in vitro are made from the blood of a human or animal and then injected into that same individual. In such situations, the antibodies produce little or no immunogenicity because the antibodies are comprised entirely of protein from that individual.

Once these primary cultures have converted to the production of antigen specific antibody, they are immortalized, for example, by fusing with human immortalized cancer cells or by transfecting the antibody producing cells with oncogenes, such as ras, or with viruses, such as Epstein Barr virus. The resultant hybridomas are screened for specific antibody secretion and then processed, for example, by limiting dilution procedures to isolate a single monoclonal antibody producing cell. The resultant human monoclonal antibody contains only human protein. No animal protein enters into the construction of the human monoclonal antibody. The absence of all animal protein ensures that no human-anti-animal antibody will result from the therapeutic administration of these antibodies.

The methods and compositions of the present invention provide a novel and versatile approach to systems for the targeted stimulation of an immune response. In one disclosed embodiment, the present invention comprises component-stimulating compositions. In a preferred embodiment, the component-stimulating compositions comprise component-specific immunostimulating agents. In another preferred embodiment, the component-stimulating compositions comprise component-specific immunostimulating agents in association with colloidal metal. In yet another preferred embodiment, such compositions comprise an antigen in combination with a component-specific immunostimulating agent, and in a further preferred embodiment an antigen and a component-specific immunostimulating agent are bound to a colloidal metal, such as colloidal gold, and the resulting chimeric molecule is presented to the immune component.

In another disclosed embodiment, the component-stimulating compositions of the invention comprise a delivery structure or platform, to which one member of a binding group is bound, and the complementary member of the binding group is bound to an antigen or is bound to a component-specific immunostimulating agent. In a more preferred embodiment, one of the complementary members of the binding group is bound to a component-specific immunostimulating agent, and another of the complementary members of the binding group is bound to a putitive antigen/vaccine. The binding group members may be selected from all such known paired binding groups including but not limited to antibody/antigen; enzyme/substrate; and streptavidin/biotin.

One embodiment of such a composition comprises a delivery structure or platform with a member of a binding group reversibly bound to it. A preferred embodiment of the present invention comprises colloidal gold as a platform that is capable of binding a member of a binding group to which component-specific immunostimulating molecules and antigen/vaccine molecules are bound to create a component-stimulating composition. In a more preferred embodiment, the binding group is streptavidin/biotin and the component-specific immunostimulating molecule is a cytokine. Embodiments of the present invention may also comprise binding the component-specific immunostimulating molecules or antigen/vaccine in a less specific method such as by using polycations.

The present invention also comprises presentation of antigen and component-specific immunostimulating agents in a variety of different carrier combinations. For example, a preferred embodiment includes administration of an antigen in association with component-specific immunostimulating agents and colloidal gold in a liposome carrier. Additional combinations are colloidal gold particles studded with viral particles which are the active vaccine candidate or are packaged to contain DNA for a putative vaccine. The gold particle may also contain a cytokine which can then be used to target the virus to specific immune cells. Such embodiments provide for an internal vaccine preparation that slowly releases antigen to the immune system for a prolonged response. This type of vaccine is especially beneficial for one-time administration of vaccines. All types of carriers, including but not limited to liposomes and microcapsules are contemplated in the present invention.

Therefore, it is an object of the invention to provide reliable and facile methods for enhancing an immune response.

It is another object of the invention to provide methods for improving vaccine efficacy.

Another object of the invention is to provide vaccines that give effective protection with only one dose administration.

Yet another object of the invention is to provide methods for the targeted stimulation of individual immune components in a specific manner.

A further object of the invention is to provide methods for the simultaneous presentation of an antigen and a component-specific immunostimulating agent to individual components of the immune system.

Another object of the present invention is to provide compositions comprising component-specific immunostimulating agents that are capable of effecting a particular component of the immune system.

Still another object of the present invention is to provide methods and compositions for suppressing the immune responses.

Another object of the present invention is to provide compositions for using simultaneous/sequential component-specific agents to initiate an immune response to a primary cancer capable of not only enhancing the immune response to the primary tumor but also mounting a systemic immune response to residual disese.

Yet another object of the present invention is to provide compositions for using simultaneous/sequential component-specific agents to initiate an immune response to a primary cancer capable of not only enhancing the immune response to the primary tumor but also mounting a systemic immune response to residual disease.

A further object of the invention to increase the antigenicity/immunogenicity of a molecule.

Still another object of the invention to generate a antigen-specific species-specific monoclonal antibody in vitro.

Yet another object of the invention to generate a wholly human monoclonal antibody through the in vitro culturing of human peripheral blood lymphocytes.

A further object of the invention is to eliminate the problem of antigen-specific species-specific induced immunity by providing a treatment for diseases with human antigen-specific antibodies.

Another object of the invention to produce a monoclonal antibody that is person specific and thereby eliminates a foreign immune response.

Yet another object of the present invention to provide reliable and versatile methods and compositions for targeting the delivery of immune enhancing agents to immune cells.

A further object of the present invention to provide methods and compositions for targeted delivery of component-specific immunostimulating agents in vitro and in vivo.

Still another object of the present invention are methods and compositions for the targeted delivery of component-specific immunostimulating agents to cells having a specific receptor.

Another object of the present invention is to provide methods and compositions comprising a targeted delivery system that is capable of binding and delivering a putitive antigen/vaccine using a component-specific immunostimulating agent.

BRIEF DESCRIPTION OF THE DRAWINGS

This patent contains at least one color photograph. Copies of this patent with the color photographs will be provided by the Patent and Trademark Office upon request and payment of the necessary fee.

FIG. 10 is a graph showing the saturable binding kinetics of the delivery platform with TNF-α.

DETAILED DESCRIPTION OF THE DISCLOSED EMBODIMENTS

Enhancement of an Immune Response

Figure 1:
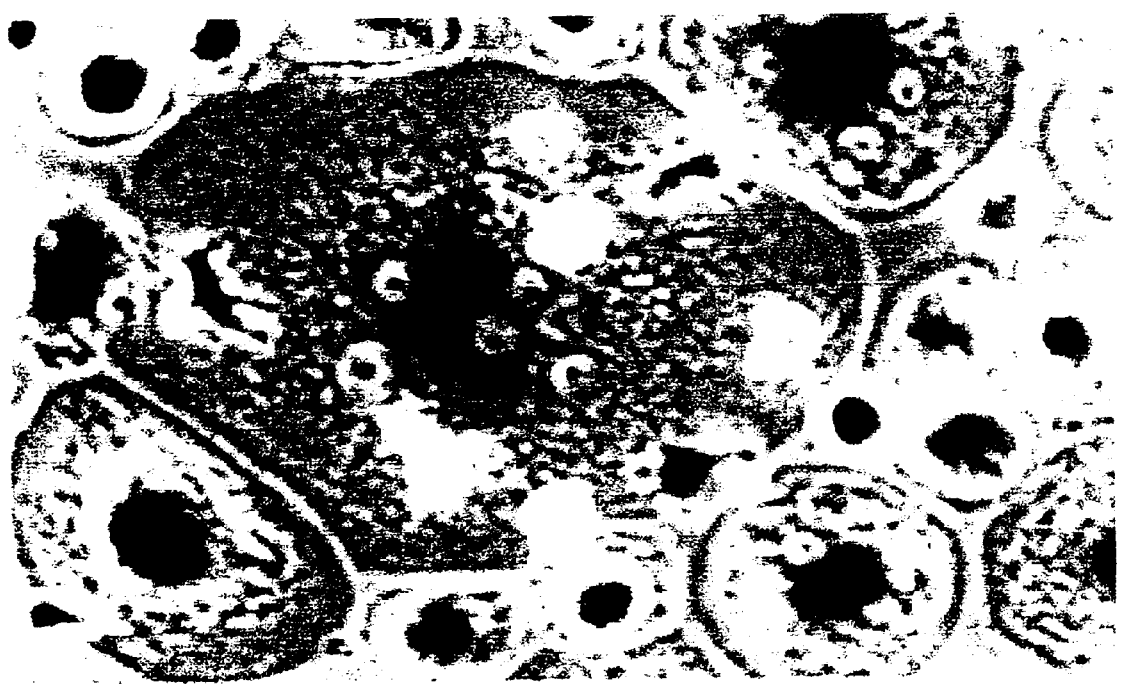
FIG. 1 illustrates the in vitro internalization of EGF/CG/IL-1β complex by macrophages.

The present invention relates to compositions and methods for enhancing an immune response and increasing vaccine efficacy through the simultaneous or sequential targeting of specific immune components. More particularly, specific immune components including, but not limited to, antigen presenting cells (APCs), such as macrophages and dendritic cells, and lymphocytes, such as B cells and T cells, are individually effected by one or more component-specific immunostimulating agents. An especially preferred embodiment provides for activation of the immune response using a specific antigen in combination with the component-specific immunostimulating agents. As used herein, component-specific immunostimulating agent means an agent, that is specific for a component of the immune system, and that is capable of effecting that component, so that the component has an activity in the immune response.

The agent may be capable of effecting several different components of the immune system, and this capability may be employed in the methods and compositions of the present invention. The agent may be naturally occurring or can be generated and manipulated through molecular biological techniques or protein receptor manipulation.

The activation of the component in the immune response may result in a stimulation or suppression of other components of the immune response, leading to an overall stimulation or suppression of the immune response. For ease of expression, stimulation of immune components is described herein, but it is understood that all responses of immune components are contemplated by the term stimulation, including but not limited to stimulation, suppression, rejection and feedback activities.

The immune component that is effected may have multiple activities, leading to both suppression and stimulation or initiation or suppression of feedback mechanisms. The present invention is not to be limited by the examples of immunological responses detailed herein, but contemplates component-specific effects in all aspects of the immune system.

The activation of each of the components of the immune system may be simultaneous, sequential, or any combination thereof. In one embodiment of a method of the present invention, multiple component-specific immunostimulating agents are administered simultaneously. In this method, the immune system is simultaneously stimulated with four separate preparations, each containing a composition comprising a component-specific immunostimulating agent. Preferably, the composition comprises the component-specific immunostimulating agent associated with colloidal metal. More preferably, the composition comprises the component-specific immunostimulating agent associated with colloidal metal of one sized particle or of different sized particles and an antigen. Most preferably, the composition comprises the component-specific immunostimulating agent associated with colloidal metal of one sized particle and antigen or of differently sized particles and antigen.

The inventors have found that they could use certain component-specific immunostimulating agents provide a specific stimulatory, up regulation, effect on individual immune components. For example, Interleukin-1β (IL-1β) specifically stimulates macrophages, while TNF-α (Tumor Necrosis Factor alpha) and Flt-3 ligand specifically stimulate dendritic cells. Heat killed *Mycobacterium butyricum* and Interleukin-6 (IL-6) are specific stimulators of B cells, and Interleukin-2 (IL-2) is a specific stimulator of T cells. Compositions comprising such component-specific immunostimulating agents provide for specific activation of macrophages, dendritic cells, B cells and T cells, respectively. For example macrophages are activated when a composition comprising the component-specific immunostimulating agent IL-1β, is administered. A preferred composition is IL-1β in association with colloidal metal, and a most preferred composition is IL-1β in association with colloidal metal and an antigen to provide a specific macrophage response to that antigen.

Many elements of the immune response are necessary for an effective vaccination. An embodiment of a method of simultaneous stimulation is to administer four separate preparations of compositions of component-specific immunostimulating agents comprising 1) IL-1β for macrophages, 2) TNF-α and Flt-3 ligand for dendritic cells, 3) IL-6 for B cells, and 4) IL-2 for T cells. The component-specific immunostimulating agent compositions may be administered by any routes known to those skilled in the art, and may use the same route or different routes, depending on the immune response desired.

In another embodiment of the methods and compositions of the present invention, the individual immune components are activated sequentially. For example, this sequential activation can be divided into two phases, the primer phase and the immunization phase. The primer phase comprises stimulating APCs, preferably macrophages and dendritic cells, while the immunization phase comprises stimulating lymphocytes, preferably B cells and T cells. Within each of the two phases, activation of the individual immune components may be simultaneous or sequential. For sequential activation, a preferred method of activation is activation of macrophages followed by dendritic cells, followed by B cells, followed by T cells. A most preferred method is a combined sequential activation wherein there is simultaneous activation of the macrophages and dendritic cells, followed by the simultaneous activation of B cells and T cells. This is an example of methods and compositions of multiple component-specific immunostimulating agents to initiate several pathways of the immune system.

The methods and compositions of the present invention can be used to enhance the effectiveness of any type of vaccine. The present methods enhance vaccine effectiveness by targeting specific immune components for activation. Compositions comprising component-specific immunostimulating agents in association with colloidal metal and antigen are used for increasing the contact between antigen and specific immune component. Examples of diseases for which vaccines are currently available include, but are not limited to, cholera, diphtheria, Haemophilus, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, and yellow fever.

The combination of route of administration and the packaging used to deliver the antigen to the immune system is a powerful tool in designing the desired immune response. The present invention comprises methods and compositions comprising various packaging methods, such as liposomes, microcapsules, or microspheres, that can provide long-term release of immune stimulating compositions. These packaging systems act like internal depots for holding antigen and slowly releasing antigen for immune system activation. For example, a liposome may be filled with a composition comprising an antigen and component-specific immunostimulating agents associated with colloidal metal. Additional combinations are colloidal gold particles studded with viral particles which are the active vaccine candidate or are packaged to contain DNA for a putative vaccine. The gold particle would also contain a cytokine which could then be used to target the virus to specific immune cells. Furthermore, one could create a fusion protein vaccine which targets two or more potential vaccine candidates and generate a vaccine for two or more applications. The particles may also include immunogens which have been chemically modified by the addition of polyethylene glycol which may release the material slowly.

The antigen/component-specific immunostimulating agent/metal complex is slowly released from the liposome and is recognized by the immune system as foreign and the specific component to which the component-specific immunostimulating agent is directed activates the immune system. The cascade of immune response is activated more quickly by the presence of the component-specific immunostimulating agent and the immune response is generated more quickly and more specifically.

Other methods and compositions contemplated in the present invention include using antigen/component-specific immunostimulating agent/colloidal metal complexes in which the colloidal metal particles have different sizes. Sequential administration of component-specific immunostimulating agents may be accomplished in a one dose administration by use of these differently sized colloidal metal particles. One dose would include four independent component-specific immunostimulating agents complexed an antigen and each with a differently sized colloidal metal particle. Thus, simultaneous administration would provide sequential activation of the immune components to yield a more effective vaccine and more protection for the population. Other types of such single-dose administration with sequential activation could be provided by combinations of differently sized colloidal metal particles and liposomes, or liposomes filled with differently sized colloidal metal particles.

Use of such a vaccination systems as described above are very important in providing vaccines that can be administered in one dose. One dose administration is important in treating animal populations such as livestock or wild populations of animals. One dose administration is vital in treatment of populations that are resistant to healthcare such as the poor, homeless, rural residents or persons in developing countries that have inadequate health care. Many persons, in all countries, do not have access to preventive types of health care, as vaccination. The reemergence of infectious diseases, such as tuberculosis, has increased the demand for vaccines that can be given once and still provide long-lasting, effective protection. The compositions and methods of the present invention provide such effective protection.

The methods and compositions of the present invention can also be used to treat diseases in which an immune response occurs, by stimulating or suppressing components that are a part of the immune response. Examples of such diseases include, but are not limited to, Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dernatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, and non-Hodgkin's lymphoma.

The present application claims priority to, and herein incorporates by reference, in their entirety, U.S. Application No. 09/189,748, filed on Nov. 10, 1998, and to U.S. Provisional Application No. 60/107,455, filed Nov. 6, 1998, and to U.S. Provisional Application No. 60/075,811, filed Feb. 24, 1998, and to U.S. Provisional Application No. 60/065,155 filed Nov. 10, 1997.

Production of In Vitro Monoclonal Antibodies

The methods and compositions of the present invention can further be used to produce antigen-specific, species-specific monoclonal antibodies that enhance immune response. These antibodies are produced, for example, by contacting in vitro an antigen, antigen presenting cells (APCs), immune cells, such as B cells, and optionally one or more component-specific immunostimulating agents. Once antigen-specific antibodies are detected, the activated immune cells are immortalized, for example, by fusing with human immortalized cancer cells. The resulting hybridomas can then be screened for specific antibody secretion and a single monoclonal antibody producing cell may then be isolated.

The antigen, APCs, immune cells, and component-specific immunostimulating agent may all be introduced into the in vitro culture at the same time. Optionally, these various components may be added sequentially in any order or combination. The antigen and component-specific immunostimulating agent may be two distinct molecules, or may be present in the form of a complex. For example, an antigen may be complexed with different cytokines, which when added in a sequential fashion would stimulate specific cells in the culture in a predictable stepwise fashion.

Cells, such as APCs and B cells may be obtained from any source, preferably from peripheral blood. Peripheral blood from any source may be used to produce the antigen-specific species-specific antibodies of the invention. Although the most significant use of the present invention is the production of human-anti-human antibodies, it is possible to use the process of the invention to develop antigen-specific species-specific antibodies for other animal species as well. For the production of human-anti-human antibodies, blood may be conveniently obtained from the American Red Cross.

In a preferred embodiment, it is desirable to separate the buffy coat from the rest of the whole blood. There are two separate components within the buffy coat that are important to the practice of the present invention. These are the antigen presenting cells (APCs), such as macrophages, lymphocytes, Langerhanns cells, and dendritic cells, and the B cells. B cells are also antigen presenting cells, but upon presentation with antigen, they produce an antibody response. Once separated from the whole blood, the entire buffy coat may be used, or the APCs and B cells may be separated and used individually. Either of these components may be isolated and frozen according to procedures well known to those of ordinary skill in the art, such as flow cytometry, magnetic cell separation, and cryopreservation, and used at a later time without affecting the generation of the antibodies.

Although any combination of antigen, antigen presenting cells (APCs), component-specific immunostimulating agents, and B cells can be employed in vitro in the present invention in any manner, a preferred preparation employs the antigen bound to a colloidal metal. In this embodiment, the buffy coat or APCs are placed in a vessel. Colloidal metal bound antigen is then added to the vessel and incubated with the buffy coat or APCs.

The antigen bound colloidal metal composition can be produced by the method described below. The antigen bound colloidal metal may be added to the buffy coat or APCs alone, or in the presence of adjuvants, immunogenic proteins, nucleotides, or accessory cytokine/immuostimulators which aid in the development of a Th2/

B-cell response. Optionally, these adjuvants, immunogenic proteins, nucleotides, and accessory cytokine/immuostimulators may be bound to the colloidal metal in a manner similar to that by which the antigen was bound prior to incubation of the colloidal metal bound antigen with the buffy coat or APCs.

If B cells are initially present, as when the entire buffy coat is used, their number may become depleted during incubation with the colloidal metal bound antigen. Therefore, after incubation, additional B cells are, optionally, added to the vessel. These B cells may be freshly obtained, frozen, or those separated from the buffy coat of the same sample. The APCs in the vessel activate the B cells to produce antibodies in response to the specific antigen bound to the colloidal metal.

Once in vitro seroconversion is confirmed, the cells are immortalized. The cells can be immortalized by several different methods, for example, by fusion with immortalized cancer cells to produce hybridomas or by transfecting the antibody producing cells with oncogenes, such as ras, or with viruses, such as Epstein Barr virus. However, any method which produces immortalized cells is contemplated by the present invention. Nonlimiting examples of immortalized cancer cell lines which are useful in the present invention are K6H6/B5 cells, HUNS-1 (U.S. Pat. No. 4,720,459), KR-12 (U.S. Pat. No. 4,693,975), WIL2-S, WI-L2-729HF2 (U.S. Pat. No. 4,594,325), UC 729-6 (U.S. Pat. No. 4,451,570), SKO-007, clone J3 of SKO-007, GK5, and LTR-228 (U.S. Pat. No. 4,624,921).

Although immortaliztion of the primary clones may be accomplished in any manner, the following is one preferred method. Immortalized cancer cells are added directly to the vessel containing the seroconverted cells. After incubation, the cells are washed in serum free DMEM (Delbecco's Minimum Essential Medium), PBS (Phosphate Buffered Saline), or any serum free physiologic buffer. The cells may then be fused, for example, using a 40% to 100% PEG solution diluted in serum free DMEM. The fused cells may then be washed and the pellet reconstituted in a 50% DMEM/RPMI media containing 10% fetal bovine serum (FBS), 10% Origen™, the antigen cocktail mentioned above and a selective media, such as the hybridoma selecting agent HAT at a final concentration of 10%. The cells are seeded into 96 well tissue culture plates in 150 µl aliquots. To increase the proliferation of clones, the cells may, optionally, be stimulated by the addition of the initial antigen or antigen/component-specific immunostimulating agent mixture such as those used in the initial immunizations.

The cells may be grown in HAT (hypozanthine, aminopterin, thymidine) containing medium for approximately two weeks. Then a nonselective media, such as HT (hypozanthine, thymidine) is substituted for the HAT as a selection drug. After another incubation of about two weeks, the cells are grown in a growth media, such as 50% DMEM/RPMI supplemented with the antigen cocktail, 10% Origen™, and 10% FBS.

The samples can be tested for the presence of antigen-specific antibodies during any of the phases of growth and are preferably tested during all phases of growth. This testing may be done by any common immunological procedure, such as RIA, EIA, ELIZA, RID, or Ouchterlony test. Positive clones are then scaled-up from 96 well plates, for example, to 6 well plates. At this point the clones can be frozen for later use.

The activity of the clones can be tested by methods known to those in the art, such as by generating ascites in pristine primed mice. The ascites are purified, and then the antibody is tested for its ability to neutralize bioactivity in a well characterized cell line, for example, the TNF sensitive cell line, WEHI 164. Clones which demonstrate neutralizing ability may then be scaled-up to generate larger quantities of purified antibody.

In another embodiment of the present invention, the buffy coat or APCs may be incubated simultaneously with the colloidal metal bound antigen and optionally an adjuvant. This type of incubation has been found to change the type of immunoresponse elicited from a Th1-like response, in which the colloidal metal antigen is associated with the APCs which may or may not contain cellular elements, to a Th2-type response in which the colloidal metal bound antigen is associated with the free-floating clusters of B cells.

Component-Stimulating Compositions

The compositions of the present invention comprise component-specific immunostimulating agents. Such a composition may comprise one component-specific immunostimulating agent or multiple component-specific immunostimulating agents. In one preferred embodiment, the composition comprises component-specific immunostimulating agents in association with colloidal metals. More preferably the compositions comprise component-specific immunostimulating agents in association with colloidal metals and other elements for specifically targeting the effect of the component-specific immunostimulating agents, including, but not limited to, antigens, receptor molecules, nucleic acids, pharmaceuticals, chemotherapy agents, and carriers.

The compositions of the present invention may be delivered to the immune components in any manner. In another preferred embodiment, an antigen and a component-specific immunostimulating agent are bound to a colloidal metal in such a manner that a single colloidal metal particle is bound to both the antigen and the immunostimulating agent. In another embodiment, multiple antigens and/or multiple component-specific immunostimulating agents are bound to a single colloidal metal particle. The combinations of antigen and component-specific immunostimulating agents, and other elements, with one or more colloidal metal particles is contemplated by the present invention. Administration of one or several of these complexed metal particles is comprised within the methods of the present invention.

In another embodiment, the component-specific immunostimulating molecules of the present invention comprise a delivery structure or platform. The component-specific immunostimulating molecule and/or the antigen/vaccine may be bound directly to the platform or may be bound to the platform through members of a binding group. A preferred embodiment of the present invention comprises a colloidal metal as a platform that is capable of binding a member of a binding group to which component-specific immunostimulating agents and putative antigen/vaccines are bound to create a targeted immune-enhancing agent. In a most preferred embodiment, the binding group is streptavidin/biotin and the component-specific immunostimulating agent is a cytokine. Embodiments of the present invention may also comprise binding the antigen/vaccine in a less specific method, without the use of binding partners, such as by using polycations or proteins.

The present invention comprises methods and compositions for targeted delivery of component-specific immunostimulating molecules that use colloidal metals as a platform. Such colloidal metals bind, either reversibly or irreversibly, molecules that interact with either an antigen/vaccine or component-specific immunostimulating agents or antigen/vaccine. The interacting molecules may either be specific binding molecules, such as members of a binding pair, or may be rather nonspecific interacting molecules that bind less specifically. The present invention contemplates the use of interacting molecules such as polycationic elements known to those skilled in the art including, but not limited to, polylysine, protamine sulfate, histones or asialoglycoproteins.

The members of the binding pair comprise any such binding pairs known to those skilled in the art, including but not limited to, antibody-antigen pairs, enzyme-substrate pairs; receptor-ligand pairs; and streptavidin-biotin. Novel binding partners may be specifically designed. An essential element of the binding partners is the specific binding between one of the binding pair with the other member of the binding pair, such that the binding partners are capable of being joined specifically. Another desired element of the binding members is that each member is capable of binding or being bound to either an effector molecule or a targeting molecule.

The compositions and methods of the present invention comprise the variations and combinations of mixtures of the above described binding capabilities and methods. For example, an embodiment of the present invention comprises the component-specific immunostimulating molecules bound directly to the metallic platform and the antigen/vaccine being bound to the metallic platform through either specific or less specific binding by integrating molecules, such as binding the binding pairs described above. Another embodiment of the present invention comprises the antigen or vaccine bound directly to the colloidal metal platform and the component-specific immunostimulating molecule bound through either specific or less specific binding by integrating molecules. In still another embodiment, the present invention comprises the binding of both the component-specific immunostimulating molecules and the antigen/vaccine to the metallic platform through specific or less specific binding by integrating molecules or the direct binding of the component-specific immunostimulating molecules and the antigen/vaccine to the metallic platform. A still further embodiment of the present invention comprises binding the component-specific immunostimulating molecules bound to the metallic platform through binding by the less specific integrating molecule binding and the antigen/vaccine bound to the metallic platform by the binding of complementary binding members. Other combinations and variations of such embodiments are contemplated as part of the present invention.

Method for Binding of Composition Components to Platform

Each of the elements of the compositions may be bound, separately or in combinations, to the colloidal metal by any method. However, a preferred method for binding the elements to the colloidal metal is as follows. In this example, the composition comprises an antigen and a component-specific immunostimulating agent, though the method is not limited to this embodiment. The antigen is reconstituted in water. Approximately 50 to 100 µg of antigen is then incubated with colloidal metal.

The pH of the colloidal antigen mixture may have to be adjusted so that it is 1–3 pH unites above the pI of the component specific agent. Subsequently, 50–100 µg of the component specific agent is added to the antigen colloidal mixture and incubated for an additional 24 hours. During this time, the targeting component specific agent becomes incorporated into the antigen gold complex resulting in an immune component targeted antigen delivery system. The inventors have successfully performed such experiments and in fact have linked up to 3 different moieties on the same colloidal metal particle.

After the binding of the component specific agent to the antigen/Au the mixture is stabilized by the addition of a 1% v/v solution of 1–100% polyethylene glycol. Other stabilizing agents may include Brij 58 and cysteine, other sulfhydryl containing compounds, phospholipids, polyvinylpyrolidone, poly-L-lysine and/or poly-L-proline. The mixture is stabilized overnight and subsequently centrifuged to separate the bound antigen and component specific agent from unbound material. The mixture is centrifuged at 14,000 rpms for 30 min., the supernatant removed and the pellet resuspended in water containing 1% albumin. This procedure has a relatively high efficiency of coupling the antigen and targeting component since 75% to 95% of both moieties are bound. Furthermore, free material which is not bound to the colloid is separated by centrifugation.

Exemplified Components

The term "colloidal metal" as used herein, includes any water-insoluble metal particle or metallic compound as well as colloids of non-metal origin such as collodial carbon dispersed in liquid or water (a hydrosol). Examples of colloidal metals which can be used in the present invention include, but are not limited to, metals in groups IIA, IB, IIB and IIIB of the periodic table, as well as the transition metals, especially those of group VIII. Preferred metals include gold, silver, aluminum, ruthenium, zinc, iron, nickel and calcium. Other suitable metals may also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form (preferably derived from an appropriate metal compound), for example, the $Al^{3+}$, $Ru^{3+}$, $Zn^{2+}$, $Fe^{3+}$, $Ni^{2+}$ and $Ca^{2+}$ ions. A preferred metal is gold, particularly in the form of $Au^{3+}$. An especially preferred form of colloidal gold is HAuCl4 (E-Y Laboratories, Inc., San Mateo, Calif.). Another preferred metal is silver, particularly in a sodium borate buffer, having the concentration of between approximately 0.1% and 0.001%, and most preferably as approximately a 0.01% solution. The color of such a colloidal silver solution is yellow and the colloidal particles range from 1 to 40 nanometers. Such metal ions may be present in the complex alone or with other inorganic ions.

Any antigen may be used in the present invention. Examples of antigens useful in the present invention include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B and other toxins, Type I Interferon, Type II Interferon, Tumor Necrosis Factor ("TNF-α"), Transforming Growth Factor-β ("TGF-β") Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-α"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE, and heat shock proteins (HSPs); mutant p53; tyrosinase; autoimmune antigens; immunotherapy drugs, such as AZT; and angiogenic and antiangiogenic drugs, such as angiostatin, endostatin, and basic fibroblast growth factor, and vascular endothelial growth factor (VEGF).

The component-specific immunostimulating agent may be any molecule or compound which increases the APC's ability to stimulate the B cell's production of antibodies. Examples of component-specific immunostimulating agents include, but are not limited to, antigens, colloidal metals, adjuvants, recqptor moelcules, nucleic acids, immunogenic proteins, and accessory cytokine/immuostimulators, pharmaceuticals, chemotherapy agents, and carriers. These component-specific immunostimulating agents may be employed separately, or in combinations. They may be employed in a free state or in complexes, such as in combination with a colloidal metal.

Adjuvants useful in the invention include, but are not limited to, heat killed *M. Butyricum* and *M. Tuberculosis*. Nonlimiting examples of nucleotides are DNA, RNA, mRNA, sense, and antisense. Examples of immunogenic proteins include, but are not limited to, KLH (Keyhole Limpet Cyanin), thyroglobulin, and fusion proteins which have adjuvant and antigen moieties encoded in the gene.

Accessory cytokine/immuostimulators include, but are not limited to, Interleukin-1 ("IL-1"), Interleukin-2 ("IL-2"), Interleukin-3 ("IL-3"), Interleukin-4 ("IL4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B and other toxins, Type I Interferon, Type II Interferon, Tumor Necrosis Factor ("TNF-α"), Transforming Growth Factor-β ("TGF-β") Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-α"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE, and HSPs; flt3 ligand/receptor system; B7 family of molecules and receptors; CD 40 ligand/receptor; and immunotherapy drugs, such as AZT; and angiogenic and anti-angiogenic drugs, such as angiostatin, endostatin, and basic fibroblast growth factor, and vascular endothelial growth factor (VEGF).

Methods and compositions, other than the use of colloidal metal, can be used to deliver the component-specific immunostimulating agents, alone or in combination with antigens or other elements. For example, the compositions may be encapsulated in a liposome or microsphere or may be delivered by means of other cell delivery vehicles, such as a viral vector. Additional combinations are colloidal gold particles studded with viral particles which are the active vaccine candidate or are packaged to contain DNA for a putative vaccine. The gold particle would also contain a cytokine which could then be used to target the virus to specific immune cells. Furthermore. one could create a fusion protein vaccine targets two or more potential vaccine candidates and generate a vaccine for two or more applications. The particles may also include immunogens which have been chemically modified by the addition of polyethylene glycol which may release the material slowly.

The component-specific immunostimulating agents may be delivered in their nucleic acid form, using known gene therapy methods, and produce their effect after translation. Additional elements for activation of immune components, such as antigens, could be delivered simultaneously or sequentially so that the cellularly translated component-specific immunostimulating agents and externally added elements work in concert to specifically target the immune response.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXPERIMENTAL DATA

Example 1

The following is the general experimental protocol that was followed for binding a molecule, whether antigen or component-specific immunostimulating agent, to colloidal gold. The molecule was reconstituted in water. 200 μg of the molecule was incubated with 25 mL colloidal gold for 24 hours. The molecule/colloidal gold complex solution was then centrifuged at 14,000 rpm for 20 minutes in a micro centrifuge at room temperature. The supernatant was then removed from the pellet.

Example 2

50 μg of epidermal growth factor (EGF) was bound to 25 ml of 40 nm colloidal gold particles at a pH of 11.0. The solution rocked on rocking platform for 24 hours. 50 μg (added as 50 μl) of targeting cytokine (i.e., IL-1β to target macrophages, IL-2 to target T cells, IL-6 to target B cells, and either TNF alpha or Flt-3 Ligand to target dendritic cells) was added to the EGF/Au solution and rocked for an additional 24 hours. To separate colloidal gold bound and unbound material the solution was then centrifuged at 14,000 rpm. The supernatant was removed and the pellet was reconstituted in 1 ml of water containing 1% human serum albumin.

Example 3

EGF was bound to colloidal gold (CG) using the procedure in Example 2. Tumor Necrosis Factor-α (TNF-α) was then bound to the EGF/CG complex using the procedure of Example 1 to produce an EGF/CG/TNF-α chimera.

Example 4

EGF was bound to colloidal gold (CG) using the procedure in Example 2. Interleukin-6 (IL-6) was then bound to the EGF/CG complex using the procedure of Example 1 to produce an EGF/CG/IL-6 chimera.

Example 5

EGF was bound to colloidal gold (CG) using the procedure in Example 2. Interleukin-2 (IL-2) was then bound to the EGF/CC complex using the procedure of Example 1 to produce an EGF/CG/IL-2 chimera.

Example 6

The buffy coat was separated from a sample of whole blood as is well known in the art. 100–500 mL of whole blood was collected on heparin. The blood was carefully layered onto a 50% (v/v) ficoll-hypaque solution and centrifuiged at 2700 rpm for 7 minutes. The buffy coat, the collection of white blood cells at the serum/ficoll interface, was collected with a Pasteur pipette and placed into 10 mL of PBS containing 0.5 mg/mL heparin. The were centrifuged at 1500 rpm and thepellet washed and recentrifuged. The cells were washed 2× in the PBS solution and centrifuged once again.

The cells were resuspended in RPMI containing either 10% fetal bovine or normal human serum and cultured in 6-well plates at a cell density of $10^6$ cells/well. The cells were then stimulated with 50–100 μL of one or all of the antigen/cytokine mixtures.

Figure 2:
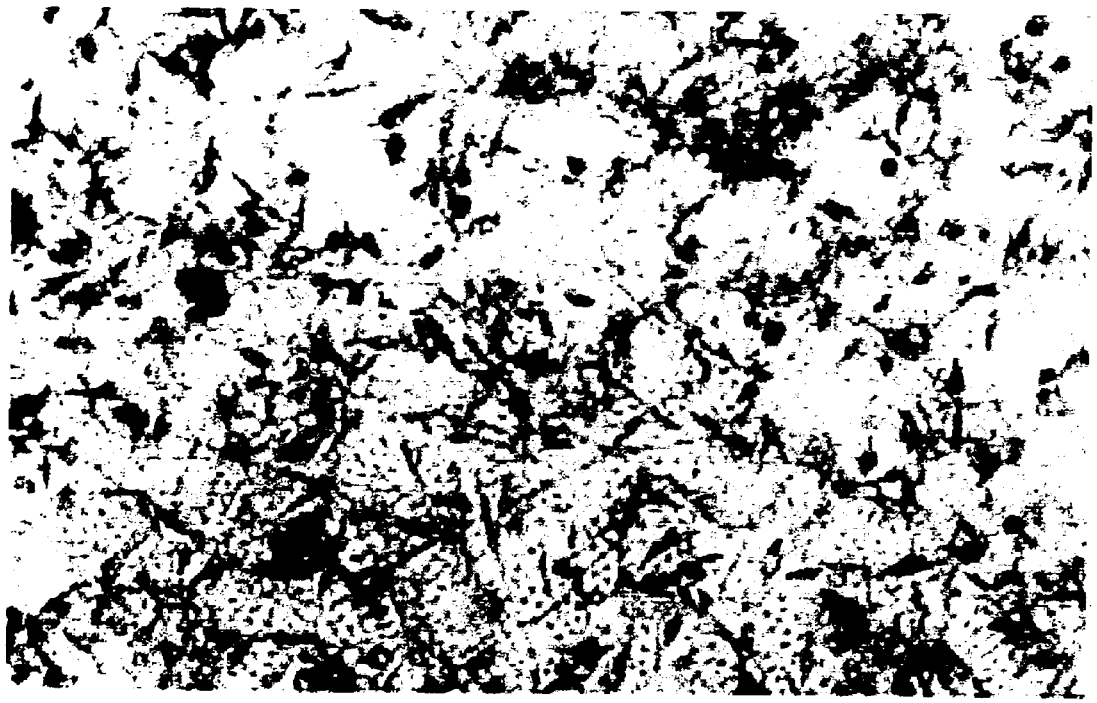
FIG. 2 illustrates the in vitro internalization of EGF/CG/TNF-α complex by dendritic cells.
Figure 3:
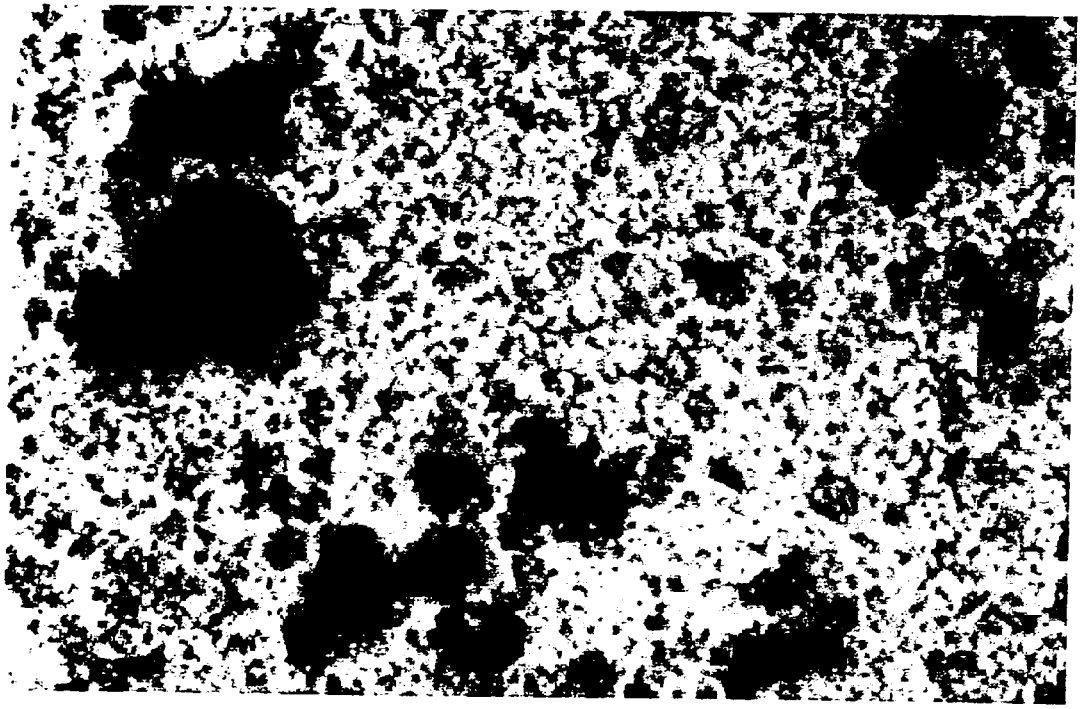
FIG. 3 illustrates the in vitro internalization of EGF/CG/IL-6 complex by B-cells.
Figure 4:
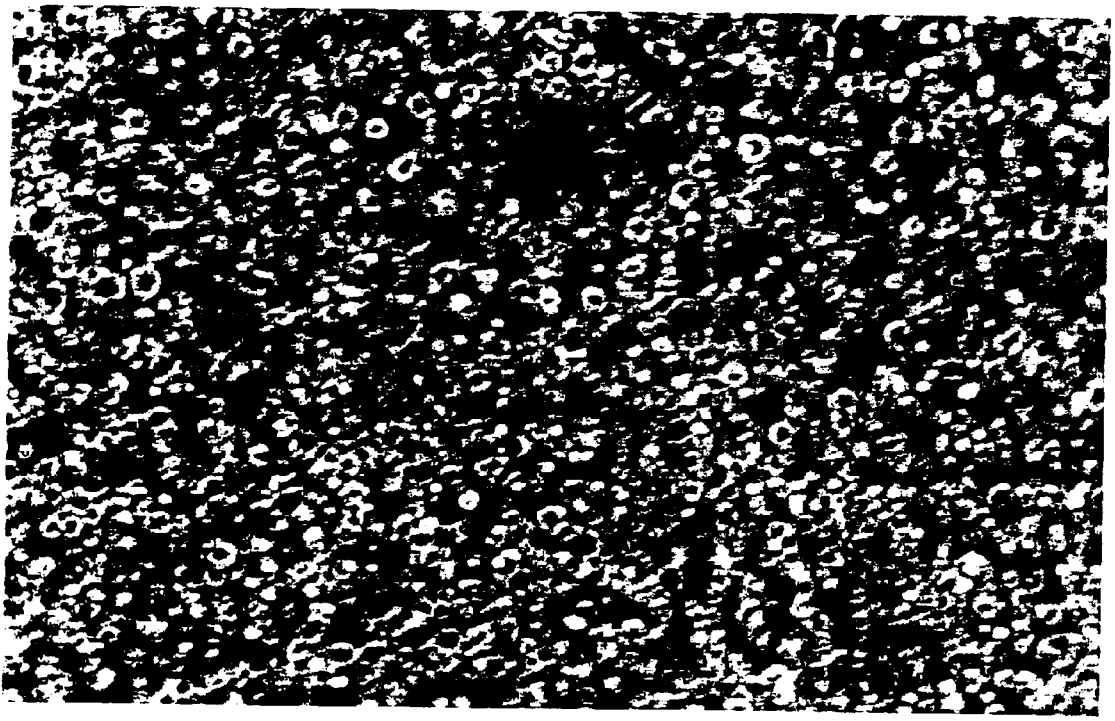
FIG. 4 illustrates the in vitro internalization of EGF/CG/IL-2 complex by T-cells.

As shown in FIG. 1, only macrophages internalized the EGF/CG/I-1β chimera, while only dendritic cells internalized the EGF/CG/TNF-α chimera (FIG. 2). Similarly, only B cells internalized the EGF/CG/IL-6 chimera (FIG. 3), and only T cells internalized the EGF/CG/IL-2 chimera (FIG. 4).

As shown by this experiment, certain component-specific immunostimulating agents are specific for individual immune components. Thus, it is possible to target specific immune components with component-specific immunostimulating agents, thereby enhancing their immune response resulting in increased activity in the overall immune response.

Example 7

For this example staphyloccal enterotoxin B was used as the putative antigen/vaccine molecule, since there is evidence that binding the toxin to colloidal gold reduces its toxicity. 500 μg of the toxin was initially bound to 250 ml of 40 nm colloidal gold particles. The colloidal solution was then aliquotted. 50 ug of a targeting cytokine (IL-1β, IL-2, IL-6 and TNFα) was added to one of the aliquots and re-incubated for 24 hours. The toxin-AU-cytokine colloid was centrifuged at 14,000 rpm and the supernatant removed. The pellet was reconstituted to 1 ml of water. The pellet was assayed for cytokine concentration by either sandwich or competitive ELISA. This was done to determine the amount of neat cytokine (unbound) that was to be injected in control animals receiving saline or toxin alone.

The immunization strategy involved simultaneous or sequential administration of neat toxin/cytokine mixture (as composition controls) or the toxin-Au-cytokine chimera. 5 mice/group were injected on days 1, 5 & 9 with either 2.5 ug neat toxin or the same dose of toxin/cytokine mixture bound to colloidal gold. During the 14 day immunization period two additional groups of mice received the neat toxin/cytokine or toxin-Au-cytokine following the schedule provided in Table 1.

TABLE 1

| Day | Group Type | Treatment Injected |
|---|---|---|
| 1 | Control | Neat toxin + Neat IL-1β + Neat TNFβ |
|   | Gold | Toxin-Au-IL-1β + Toxin-Au-TNFα |

TABLE 1-continued

| Day | Group Type | Treatment Injected |
|---|---|---|
| 5 | Control | Neat toxin + Neat IL-6 |
|   | Gold | Toxin-AU-IL-6 |
| 9 | Control | Neat toxin + Neat IL-2 |
|   | Gold | Toxin-AU-IL-2 |

All groups were rechallenged with 1 μg of neat toxin alone on day 30. Protective immunization was demonstrated by the reduced or lack of ability of the neat toxin to induce morbidity. The key observation is that the toxin bound to colloidal gold greatly reduced the toxicity of the toxin. Secondly, serum antibody titers to the toxin were 10× higher than those receiving neat treatment alone. However, the serum antibodies of animals receiving the sequential treatment were 100 times greater than the animals receiving the neat treatment. Finally, upon the rechallenge with the neat toxin 100% of the animals treated with toxin died whereas only 20% fatality was observed in the simultaneous group.

Thus the compositions and methods of the present invention can be used to increase the efficacy of a vaccine.

Example 8
Binding of Cytokine to Colloidal Gold

Human TNF-α was reconstituted in water at a pH of 11 to a final concentration of 1 ug/ml. 300 ug of recombinant human TNF-α was incubated overnight with 25 ml of 30–40 nm colloidal gold particles on a rocking platform while mixing.

The 25 ml of colloidal gold bound TNF-α solution was divided in half. One aliquot was blocked with 125 μl of 100% PEG solution. The other aliquot was not blocked. The two aliquots were placed back on the rocking platform and incubated an additional 1 to 5 days.

The two aliquots were then centrifuged at 14,000 rpm for 20 minutes. The supernatant was then removed from the pellet. The pellets were blocked by reconstitution with 10 ml of a 1% solution of human serum albumin (HSA) in water at apH of 11.

The aliquots were mixed on a rocking platform for 6 hours. The aliquots were then centrifuged at 14,000 rpm for 20 minutes and reconstituted in 3.5 ml of 1% HSA in water at a pH of 11.

Example 9
Generation of Human-Anti-Human INF-α Antibodies

The buffy coat was separated from peripheral blood by ficollation and washed with PBS containing 0.5 mg/ml heparin and EDTA. The cells were placed into 10-T-75 culture flasks. The cells were cultured for two weeks in RPMI with ten percent (10%) heat inactivated fetal bovine serum, ten percent (10%) ORIGEN™ and 100 ng/ml of cytokine cocktail which is composed of the TNF-α/colloidal gold complex of Example 8 along with the following cytokines: IL-4, IL-6, IL-7, IL-10, IL-11, stem cell factor ("SCF"), GMCSF, and GSF, both alone and bound to colloidal gold.

Example 10
ELISA Assay for Human-Anti-Human TNF-α Antibodies 1 ml aliquots were taken from three of the flasks of cells treated as shown in Example 9 and centrifuged at 1,500 rpm for 15 minutes. The supernatant was collected and stored at −20° C.

Recombinant human TNF was coated onto the wells of a microtiter plate in a carbonate/bicarbonate buffer. The plate was washed four times with TBS having 2.0 ml/l Tween 20. 100 μl of the supernatant was added to each well. Control wells received unused growth medium. The samples were incubated overnight at room temperature.

The plates were then washed and 100 μl of an alkaline-phosphatase conjugated goat-anti-human IgG, diluted 1:1000 (in TBS+0.1% BSA), was incubated with the wells for 1 hour. The plates were then rewashed and 100 μl of the alkaline phosphatase substrate (pNPP) was incubated with the wells until appropriate color developed.

Figure 5:
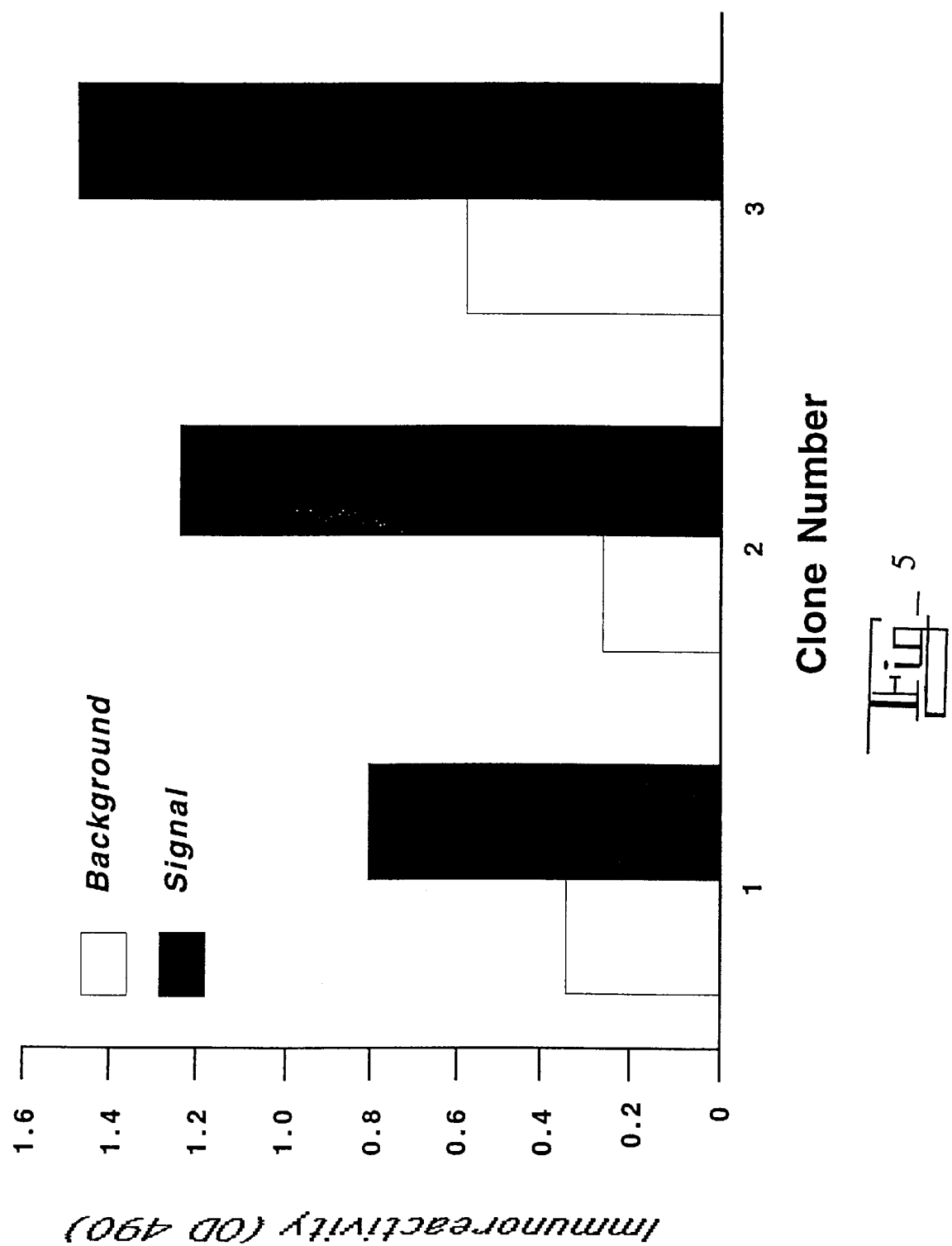
FIG. 5 illustrates the production of human-anti-human TNF-α antibodies by the process of the invention.

The results of this assay are illustrated in FIG. 5. This figure shows that human-anti-human TNF-α antibodies were produced by the method of the invention as described in Examples 8 and 9.

Example 11
Cell Fusion and Hybridoma Selection

Once in vitro seroconversion of the cells in Example 9 was confirmed, $10^6$–$10^7$ K6H6/B5 myeloma cells were added directly into the vessel in which the seroconverted cells were detected. The cells were gently mixed, collected and centrifuged at 1,200 rpm for 15 minutes. The supernatant was removed, and the pellet washed in serum free DMEM. The cells were centrifuged one last time, and the supernatant completely removed. The pellet was gently tapped loose, and the cells fused by the addition of a 53% PEG 1450 solution according to the strategy described in the table below.

The PEG solution was added to the cells using the following method and incubations, while shaking the cells at 37° C.:

| Time | Volume of a PEG added (dropwise) |
| --- | --- |
| 0 min | 0.5 ml over 30 seconds and wait 30 seconds |
| 1 min | 0.5 ml over 30 seconds and wait 30 seconds |
| 2 min | 1.0 ml over 60 seconds and wait 60 seconds |

Next, serum free DMEM was added to the cells using the following schedule.

| Time | Volume of DMEM added (dropwise) |
| --- | --- |
| 0 min | 1.0 ml over 30 seconds and wait 30 seconds |
| 4 min | 1.0 ml over 30 seconds and Wait 30 seconds |
| 5 min | 8.0 ml over 60 seconds and wait 60 seconds |
| 7 min | 15.0 ml over 60 seconds and incubate 1 minute |

The cells were subsequently centrifuged at 1,200 rpm for 15 minutes. The supernatant was removed, and the pellet was reconstituted in a 50% DMEM/RPMI media containing 10% FBS, 10% Origen™, the cytokine cocktail mentioned above and the hybridoma selecting agent HAT at a final concentration of 10%. The cells were initially seeded into five 96 well tissue culture clusters in 150 μl aliquots. To increase the proliferation of clones, the cells were also stimulated with 25 μl colloidal gold bound TNF-α used in the initial immunizations.

The cells were grown in HAT containing medium for two weeks, after which HT was substituted for the HAT as a selection drug. Following two weeks of growth, the cells were grown in 50% DMEM/RPMI media supplemented with the cytokine cocktail, 10% Origen™, and 10% FBS.

Example 12
Testing of Supernatants for Positive Antibody Function

The presence of TNF-α-specific antibodies in the samples in Example 13 was tested during all phases of the growth. The supernatants were initially tested by direct EIA and then by an in vitro assay which measures the inhibition of proliferation of WEHI cells in a dose-dependent manner by TNF-α. Positive clones were scaled-up from original 96 well plates to 6 well plates. Subsequently, all clones testing positive were scaled-up for cryopreservation, as well as the generation of 5 ml of ascites in pristine primed mice. The ascites were purified, and the antibody tested for its ability to prevent the inhibition of proliferation of WEHI cells by TNF-α. The ability of the purified antibody to block bioactivity indicated its neutralizing activity.

Clones demonstrating neutralizing activity were scaled-up to generate 10–100 mg of purified antibody. These antibodies were initially screened for the in vivo neutralization of exogenously administered TNF-α.

Example 13
Effect of Colloidal Gold Bound TNF-α on Cell Surface Markers Determined by Flow Cytometry Buffy coats were obtained from the American Red Cross and were separated using ficol. The lymphocytes were washed 3 times with PBS containing 0.2 mg/ml heparin and again treated with ficol. After washing, 1–5 million cells per well were seeded in 9–12 well tissue culture clusters in DMEM supplemented with 10% FBS.

Each well contained 2 ml of either (1) media alone, (2) 0.5 ug/ml of the mitogen phytohemaglutinin (PHA) (for the induction of a T cell response), (3) 1.0 ug/ml of the mitogen lipopolysaccharides (L,PS) (for the induction of an inflammatory response), or (4) a combination of the mitogens LPS & PHA each at a final concentration of 0.5 & 1.0 ug/mI, respectively. Note that it is possible to use other mitogens, such as Pokeweed mitogens, as well as other agents including superantigens, such as staphylococcal enterotoxin A and B in this assay. The ills were stimulated with either mitogens (PHA or LPS) alone, or mitogens in the presence of either gold/TNF-α which has been stabilized with polyethylene glycol (PEG) in HSA (human serum albumin) or gold/TNF-α which has been treated with HSA alone. The culture plates were harvested for flow cytometric analysis of the cell surface, cell activation markers, and cytokine expressions.

The cells were analyzed for changes in their CD4, CD8 and CD19 levels as well as activational marker CD69 using a Beckton Dickinson Facscalibur and the Becton Dickinson tritest MAB set. This was done by collecting the cells, centrifuging, and removing 1.8 ml of supernatant. The cells were titurated, i.e., the cellular pellet was resuspended, and 75 μl samples were incubated with the appropriate MAB according to the manufacturer's instructions.

Although flow cytometry did not detect any differences in the CD4, CD8 or CD19 levels between the control and gold treated cells 24–48 hours after treatment, visual inspection of the plates revealed that cluster-like formations had formed in both naive and gold treated cells. Yet, in the cells treated with colloidal gold conjugated TNF-α, the number of clusters appeared larger and in greater frequency and cell density. More interestingly the surrounding cells appeared to migrate toward the gold treated clusters. This may reflect the TNF-α leaching off the gold because there was a definite gradation of cell migration. In addition, the cellular migration was not as striking in cells treated with PEG-stabilized gold bound TNF-α, indicating that the TNF was not leaching off the gold or leaching off to a much lower degree.

Forty-eight hours after mitogen treatment typical conditioning of the media induced by the stimulation of the white blood cells with PHA was observed. However, the cells in the wells treated with gold bound TNF-α that is stabilized with PEG or that is unstabilized exhibited significantly less conditioning of the media, indicating that the gold/TNF-α was blocking the PHA-induced mitogenesis. This may indicate that the colloidal gold blocks a Th1-like T cell response.

Although flow cytometric analysis did not reveal any significant changes in CD4, CD8, or CD19 cell populations within 24–48 hours after stimulation, trafficking of the colloidal gold bound TNF-α into several cell types was observed. While control cells had a normal transparent phenotype, the stabilized and unstabilized gold treated cells had concentrations of the gold stain in several bcations on the cells as well as cell clusters. The distribution of the gold was varied from a central intracellular location to the cell surface. Also, the material appeared in multiple cell types, including rounded as well as dendritic cells. In rounded cells the localization of the gold material was either in the nucleus or on one side of the cell surface. Although not identified by cell surface markers, the rounded cells are thought to be differentiating monocytes/macrophages because of their ability to form giant cells. (FIGS. 6a and 6b) The colloidal gold stain disappeared with time and, therefore, does not appear to be permanent. This indicates that the colloidal gold/TNF-α mixture was being metabolized once it entered the cell. However, the cells retained their ability to uptake colloidal gold since the stain reappeared upon restimulation with colloidal gold bound TNF-α.

Figure 6A:
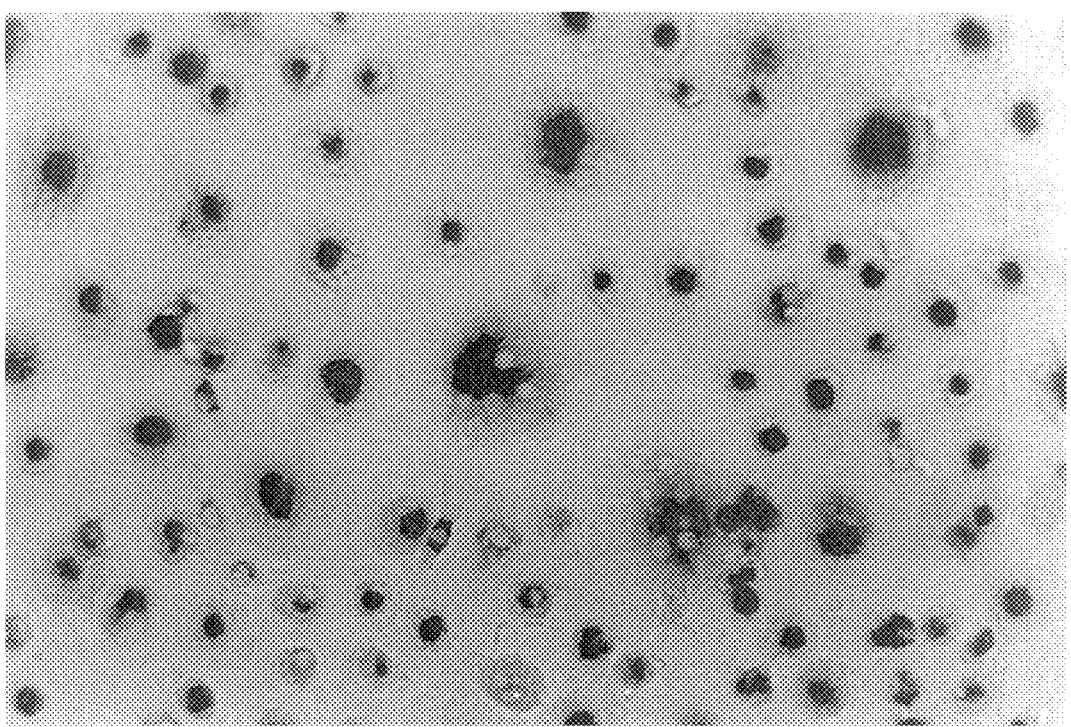
FIG. 6a is a 200× bright field micrograph illustrating the giant cell formation induced by this long term incubation of isolated human lymphocytes with colloidal gold/TNF-α.
Figure 6B:
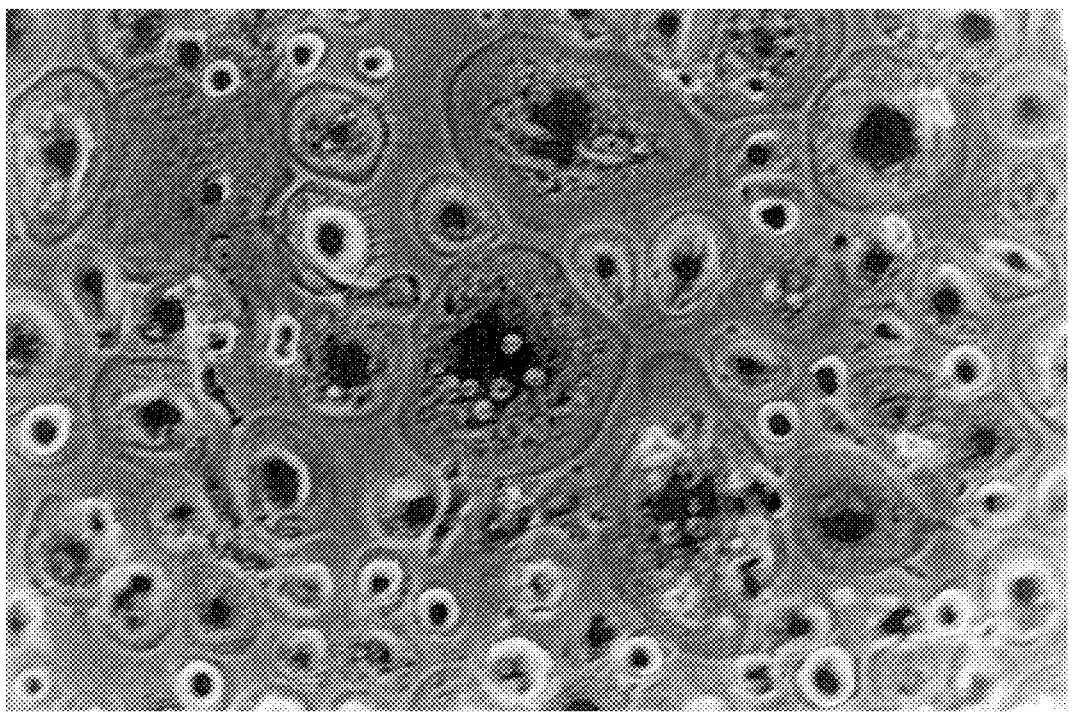
FIG. 6b is a 200× phase contrast micrograph bright field monograph of the same cells.

FIG. 6a is a 200× bright field micrograph illustrating the giant cell formation induced by this long term incubation of isolated human lymphocytes with colloidal gold/TNF-α. FIG. 6b is a 200× phase contrast micrograph bright field monograph of the same cells.

Example 14

Lymphocytes were isolated from the buffy coats of human peripheral blood obtained from the American Red Cross. The lymphocytes were treated with either (1) colloidal gold alone, (2) colloidal gold bound with human serum albumin (HSA), or (3) colloidal gold bound with TNF-α. Each group was divided into two aliquots. One aliquot was blocked with 1% PEG, and the other remained untreated.

Figure 7:
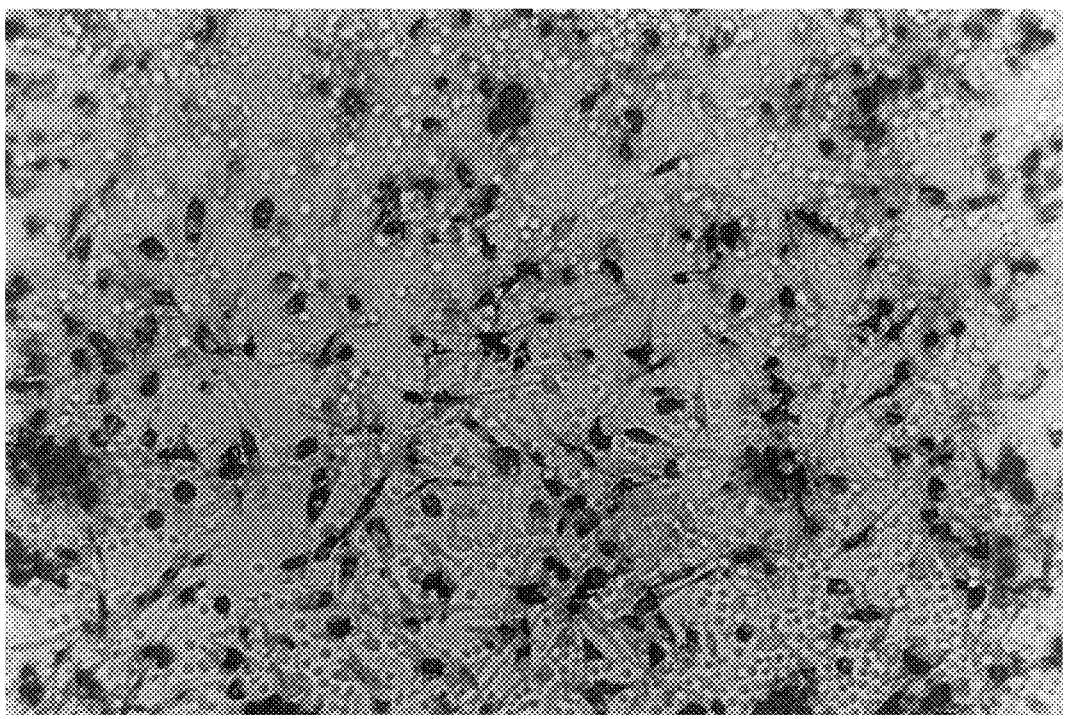
FIG. 7 demonstrates the necessity of the colloidal gold to generate an antibody response to self proteins.

The primary cell type which took up the gold or gold/HSA group was the macrophage. This was confirmed by giant cell formation. However, as illustrated by FIG. 7, the primary cell type taking up the gold in the TNF-α/gold group had the elongated form of dendritic cells.

This result is indicative of receptor mediated binding of the colloidal gold bound TNF-α. Additionally, the requirement of TNF-α for the differentiation of dendritic cells suggests that the colloidal gold bound TNF-α retained its biologic activity.

Example 15

This experiment was designed to determine the effect of adjuvant components on the uptake of colloidal gold by isolated lymphocytes. The experiment was performed in the same manner as Examples 6 and 7, except that an additional group of cells was included. These cells received 100 µl of a 1.0 mg/ml suspension of heat killed *Mycobacterium Butyricum*. This bacteria is routinely used in adjuvant preparation for antibody generation.

Figure 8:
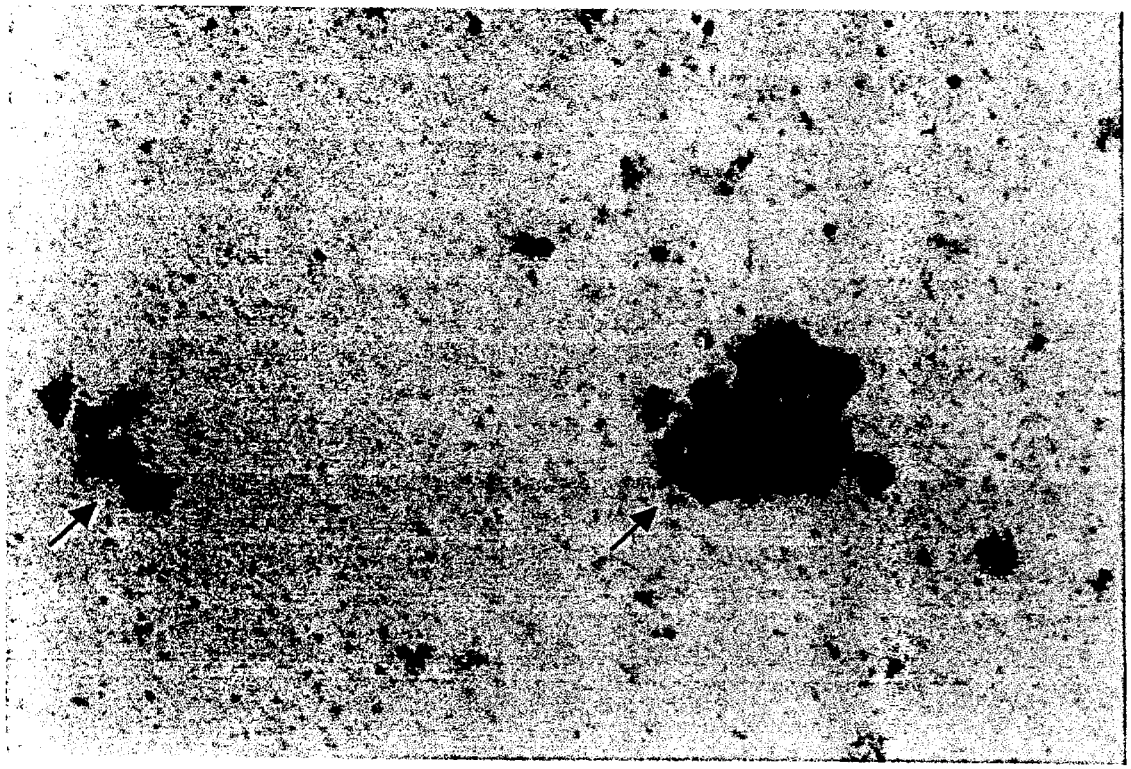
FIG. 8 illustrates that the gold stain is associated with frefloating clusters of activated B-cells, not macrophages or dendritic cells.
Figure 9:
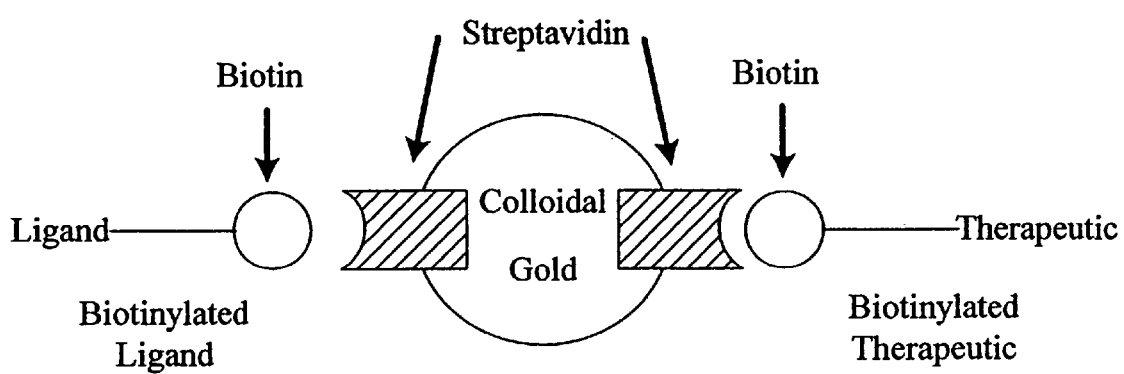
FIG. 9 is a schematic drawing of a preferred embodiment of the present invention.

As illustrated in FIG. 8, the gold stain was no longer associated with either the macrophage or dendritic cells, but was associated with frefloating clusters of cells, which may be activated B-cells. Phenotypying studies are currently underway to confirm this hypothesis.

Example 16

Streptavidin bound to colloidal gold exhibited saturable binding kinetics. For this experiment 500 μg streptavidin was bound to 50 ml of 32 nm colloidal gold for 1 hour. Subsequently, 5 ml of a stabilizing solution (5% PEG 1450,0.1% BSA) was added to the tube and allowed to mix for an additional 30 mm. The sol was centrifuged to remove unbound streptavidin and washed 2 times with 5 ml of the stabilizing solution. After a final spin, the pellet was reconstituted to a volume of 5 ml with the stabilizing solution. 1 ml aliquots were distributed to microfuge tubes. To these tubes increasing amounts of biotinylated human TNF alpha were added. The biotinylated cytokine was incubated with the streptavidin gold for 1 hour. The material was centrifuged at 10,000 rpms for 10 mm. The resultant supernatant was collected and saved for TNF determinations. The pellets from each tube were washed 1 time with stabilizing solution and recentrifuged. The supernatant from this spin was discarded. The pellet was reconstituted to 1 ml with stabilizing solution and both the pellet and initial supernatant were assayed for TNF concentrations using our CYTELISA™ TNF kit. One can see that greater than 90% of the biotinylated TNF immunoreactivity was found in the pellet (FIG. 10.) indicating that the biotinylated TNF was captured by the streptavidin bound gold.

Example 17

This experiment was to evaluate the feasibility of the streptavidin gold complex as a targeted drug delivery system. In order for this occur the streptavidin conjugated colloidal gold must bind both a biotinylated targeting ligand as well as a biotinylated therapeutic. To investigate this, we performed the following experiment.

100 ml of a 32 nm colloidal gold solution was bound with a saturating concentration of streptavidin. After 1 hour the sol was centrifuged and washed as described above. The colloidal gold bound streptavidin was then bound with sub-saturating concentrations of biotinylated cytokine. The material was vortexed and incubated for 1 hour at room temperature. Afterwards the sol was centrifuged and the pellet incubated with a solution of biotinylated polylysine. After a 1 hour incubation, the sol was re-centrifuged and washed. After a final spin and resuspension (the final volume of the sol was approximately 1 ml) 50 μg of the βgalactosidase reporter gene was incubated with the concentrated streptavidin/biotinylated cytokine/polylysine chimera for 1 hour. The material was centrifuged to remove unbound plasmid DNA. The final construct (biotin EGF-SAP-Au-biotin polylysine-DNA) was centrifuged at 14,000 rpms. The supernatant was assayed for the presence of DNA by determining its OD at 260 nm. We observed a decrease in the supernatant OD @ 260 nm from 0.95 to 0.25 after the incubation of the plasmid DNA with the biotin EGF-SAP-Au-biotin polylysine construct. The DNA was bound by the biotin EGF-SAP-Au-biotin polylysine-DNA and was centrifuged out of the sol into the pellet. These data show that a new drug delivery system was developed using avidin binding to colloidal gold. Biotinylation of the targeting and delivery payload was then used as the method for binding these molecules to the colloidal gold based drug/gene delivery system.

It should be understood, of course, that the foregoing relates only to preferred embodiments of the present invention and that numerous modifications or alterations may be made therein without departing from the spirit and the scope of the invention as set forth in the appended claims.

We claim:

1. A method for affecting an immune response, comprising, administering a composition comprising colloidal metal particles, an antigen, and at least one component-specific immunostimulating agent, wherein the component-specific immunostimulating agent is interleukin-1β (IL-1β), tumor necrosis factor-α (TNF-α), Flt-3 ligand, interleukin-6 (IL-6), heat killed *Mycobacterium butyricum*, or interleukin-2 (IL-2).

2. The method of claim 1, wherein the antigen comprises interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-10 (IL-10), interleukin-11 (IL-11), interleukin-12 (IL-12), interleukin-13 (IL-13), lipid A, phospholipase A2, endotoxins, staphylococcal enterotoxin B, Type I Interferon, Type II Interferon, tumor necrosis factor a (TNF-α), transforming growth factor-β (TGF-β), lymphotoxin migration inhibition factor, granulocyte-macrophage colony-stimulating factor (CSF), monocyte-macropahge CSF, granulocyte CSF, vascular epithelial growth factor (VEGF), angiogenin, transforming growth factor (TGF-α), heat shock proteins (HSPs), carbohydrate moieties of blood groups, Rh factors, fibroblast growth factor, nucleotides, DNA, RNA, mRNA, MART, MAGE, BAGE, mutant p53, tyrosinase, AZT, angiostatin, endostatin, or a combination thereof.

3. The method of claim 1, wherein administering the composition comprises sequentially activating a primer phase and an immunization phase of the immune response.

4. The method of claim 3, wherein activating the primer phase comprises the stimulation of antigen presenting cells selected from a group consisting of macrophages, dendritic cells and B cells.

5. The method of claim 3, wherein activating the primer phase comprises the activation of macrophages and dendritic cells.

6. The method of claim 3, wherein activating the immunization phase comprises the stimulation of lymphocytes selected from a group consisting of B cells and T cells.

7. The method of claim 3, wherein activating the primer phase and the immunization phase comprise a simultaneous activation of macrophages and dendritic cells followed by a simultaneous activation of B cells and T cells.

8. The method of claim 1, wherein the method stimulates the immune response.

9. The method of claim 1, wherein the method suppresses the immune response.

10. A method for enhancing vaccine efficacy comprising administering a composition comprising colloidal metal particles, an antigen, and at least one component-specific immunostimulating agent, wherein the component-specific immunostimulating agent is interleukin-1β (IL-1β), tumor necrosis factor-α (TNF-α), Flt-3 ligand, interleukin-6 (IL-6), heat killed *Mycobacterium butyricum*, or interleukin-2 (IL-2).

11. The method of claim 10, wherein the antigen comprises interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-10 (IL-10), interleukin-11 (IL-11), interleukin-12 (IL-12), interleukin-13 (IL-13), lipid A, phospholipase A2, endotoxins, staphylococcal enterotoxin B, Type I Interferon, Type II Interferon, tumor necrosis factor α (TNF-α), transforming growth factor-β (TGF-β), lymphotoxin migration inhibition factor, granulocyte-macrophage colony-stimulating factor (CSF), monocyte-macropahge CSF, granulocyte CSF, vascular epithelial growth factor (VEGF), angiogenin, transforming growth factor (TGF-α), heat shock proteins (HSPs), carbohydrate moieties of blood groups, Rh factors, fibroblast growth factor, nucleotiudes, DNA, RNA, mRNA, MART, MAGE, BAGE, mutant p53, tyrosinase, AZT, angiostatin, endostatin, or a combination thereof.

12. The method of claim 10, wherein the administering of component-specific immunostimulating agents comprises sequential administration of component-specific immunostimulating agents.

13. The method of claim 10, wherein the colloidal metal particles are of different sizes.

14. The method of claim 13, wherein administering the component-specific stimulating agent, the antigen, and the colloidal metal particles of different sizes comprises simultaneously administering the component-specific stimulating agent, the antigen and the colloidal metal particles of different sizes as a single dose.

15. The method of claim 10, wherein administering the component-specific stimulating agent, colloidal metal particles, and an antigen comprises oral, intramuscular, or parenteral administration.

16. The method of claim 10, wherein administering the component-specific immunostimulating agent, colloidal metal particles, and an antigen comprises administration with a carrier molecule.

17. The method of claim 10, wherein the carrier molecule comprises liposomes, microcapsules, microspheres or a combination thereof.

18. The method of claim 10, wherein the method is used to stimulate or suppress immune components in the treatment of disease, wherein the disease is cancer, allergic rhinitis, eczema, urticaria, anaphylaxis, transplant rejection, systemic lupus erthymatosus, rheumatoid arthritis, seronegative spondyloarthritides, Sjogren's syndrome, systemic sclerosis, polymyositis, dermatomyositis, Type I Diabetes Mellitus, Acquired Immune Deficiency Syndrome, Hashimoto's thyroiditis, Graves' disease, Addison's disease, polyendocrine autoimmune disease, hepatitis, sclerosing cholangitis, primary biliary cirrhosis, pernicious anemia, coeliac disease, antibody-mediated nephritis, glomerulonephritis, Wegener's granulomatosis, microscopic polyarteritis, polyarteritis nodosa, pemphigus, dermatitis herpetiformis, psoriasis, vitiligo, multiple sclerosis, encephalomyelitis, Guillain-Barre syndrome, Myasthenia Gravis, Lambert-Eaton syndrome, sclera, episclera, uveitis, chronic mucocutaneous candidiasis, Bruton's syndrome, transient hypogammaglobulinemia of infancy, myeloma, x-linked hyper IgM syndrome, Wiskott-Aldrich syndrome, ataxia telangiectasia, autoimmune hemolytic anemia, autoimmune thrombocytopenia, autoimrune neutropenia, Waldenstrom's macroglobulinemia, amyloidosis, chronic lymphocytic leukemia, or non-Hodgkin's lymphoma.

* * * * *